United States Patent
Sano et al.

(10) Patent No.: US 11,175,241 B2
(45) Date of Patent: Nov. 16, 2021

(54) X-RAY PHASE IMAGE CAPTURING SYSTEM

(71) Applicant: Shimadzu Corporation, Kyoto (JP)

(72) Inventors: Satoshi Sano, Kyoto (JP); Kenji Kimura, Kyoto (JP); Taro Shirai, Kyoto (JP); Masanobu Sato, Kyoto (JP); Takahiro Doki, Kyoto (JP); Akira Horiba, Kyoto (JP); Naoki Morimoto, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 16/767,528

(22) PCT Filed: Nov. 27, 2018

(86) PCT No.: PCT/JP2018/043465
§ 371 (c)(1),
(2) Date: May 27, 2020

(87) PCT Pub. No.: WO2019/138705
PCT Pub. Date: Jul. 18, 2019

(65) Prior Publication Data
US 2021/0148839 A1    May 20, 2021

(30) Foreign Application Priority Data
Jan. 12, 2018  (JP) .............................. JP2018-003803

(51) Int. Cl.
*G01N 23/041* (2018.01)
*A61B 6/00* (2006.01)
*G01B 11/25* (2006.01)

(52) U.S. Cl.
CPC ........... *G01N 23/041* (2018.02); *A61B 6/484* (2013.01); *G01B 11/25* (2013.01)

(58) Field of Classification Search
CPC ........... G01N 23/041; G01N 23/20075; G01N 23/20025; G01N 23/04; G01N 23/046;
(Continued)

(56) References Cited

U.S. PATENT DOCUMENTS

2010/0220832 A1* 9/2010 Ning ................... A61B 6/027
378/4
2011/0243302 A1* 10/2011 Murakoshi ........... G01N 23/041
378/62
(Continued)

FOREIGN PATENT DOCUMENTS

WO    2009/104560 A    8/2009

OTHER PUBLICATIONS

Written Opinion for PCT application PCT/JP2018/043465 dated Feb. 19, 2019, submitted with a machine translation.

*Primary Examiner* — David P Porta
*Assistant Examiner* — Mamadou Faye
(74) *Attorney, Agent, or Firm* — Muir Patent Law, PLLC

(57) ABSTRACT

This X-ray phase image capturing system (100) includes an X-ray source (1), a plurality of gratings, and a detector (4), a moving mechanism (8), and an image processing unit (5). The image processing unit (5) is configured to generate a phase-contrast image (15) based on a plurality of feature quantities (12) and feature quantities 14 extracted from a plurality of X-ray image sets (R) acquired by performing fringe scanning a plurality of times in a short time.

13 Claims, 15 Drawing Sheets

First Embodiment

(58) Field of Classification Search
CPC ...... G01N 23/207; A61B 6/484; G01B 11/25; G01T 1/20; G01T 1/2018; G21K 1/067
See application file for complete search history.

(56) References Cited

U.S. PATENT DOCUMENTS

| | | | |
|---|---|---|---|
| 2013/0011040 A1* | 1/2013 | Kido | G01N 23/04 382/132 |
| 2014/0126690 A1* | 5/2014 | Yamaguchi | A61B 6/484 378/36 |
| 2015/0178905 A1* | 6/2015 | Fletcher | G06K 9/4604 382/132 |
| 2016/0125599 A1* | 5/2016 | Stampanoni | G06T 7/0012 382/131 |

* cited by examiner

First Embodiment

First Embodiment

First Embodiment

(A) Feature quantity data (a) Absorption image  (b) Phase differential image  (c) Dark-field image

(B) Second feature quantity (a) Absorption image  (b) Phase differential image  (c) Dark-field image

(C) Phase contrast image (a) Absorption image  (b) Phase differential image  (c) Dark-field image

First Embodiment

Second Modification of First Embodiment

X-RAY PHASE IMAGE CAPTURING SYSTEM

TECHNICAL FIELD

The present invention relates to an X-ray phase image capturing system, and more particularly to an X-ray phase image capturing system that performs imaging using a plurality of gratings.

BACKGROUND OF THE INVENTION

Conventionally, an X-ray phase image capturing system that performs imaging using a plurality of gratings is known. Such an X-ray phase difference image capturing system is disclosed, for example, in International Publication No. WO 2009/104560.

The X-ray phase image capturing system disclosed in International Publication No. WO 2009/104560 is configured to generate a phase-contrast image by a fringe scanning method by performing X-ray imaging using a Talbot interferometer.

Here, in a Talbot interferometer, imaging is performed using a phase grating and an absorption grating. Specifically, the imaging is performed a plurality of times while translating one of a plurality of gratings in a direction perpendicular to the grating pattern. A fringe scanning method is a method of generating a phase-contrast image based on an intensity change of a pixel value of each pixel of X-ray images captured a plurality of times while translating a grating. A phase-contrast image includes an absorption image, a phase differential image, and a dark-field image. The absorption image is an image acquired by imaging based on attenuation of X-rays that occurs when the X-rays pass through a subject. The phase differential image is an image acquired by imaging based on a phase deviation of X-rays that occurs when X-rays pass through a subject. The dark-field image is a visibility image acquired by a change in visibility based on small-angle scattering of an object. The dark-field image is also called a small-angle scattering image. "Visibility" refers to sharpness.

In a Talbot interferometer, a phase grating is irradiated with highly coherent X-rays to image the inner structure of a subject based on a Moire fringe formed by interfering an absorption grating with a self-image of the phase grating formed at a predetermined position. In generating a phase-contrast image using a fringe scanning method, a phase-contrast image is generated based on a waveform of an intensity change of a pixel value of each pixel of a Moire fringe imaged while translating a phase grating or an absorption grating by at least one period of the grating in a direction perpendicular to the grating pattern.

PRIOR ART DOCUMENT

Patent Document
Patent Document 1: International Publication No. WO 2009/104560

SUMMARY OF THE INVENTION

Problems to be Solved by the Invention

However, in the Talbot interferometer used in the X-ray phase image capturing system described in International Publication No. WO 2009/104560, a phase-contrast image is generated based on an intensity change of a pixel value of each pixel of a plurality of X-ray images. For this reason, when performing imaging while translating a grating by one period of the grating, in cases where a movement other than a translation movement for fringe scanning occurred in at least one of the plurality of gratings, the waveform of the acquired intensity change changes. Furthermore, in cases where a focal point deviation occurs in an X-ray source when performing imaging while translating a grating by one period of the grating, the position of the self-image of the phase grating moves, and therefore, the waveform of the acquired intensity change changes. Furthermore, in cases where the grating is thermally deformed due to the heat from the X-ray source and/or the outside, the period of the grating fluctuates, and therefore, the waveform of the acquired intensity change changes. That is, in cases where a positional deviation other than the positional deviation due to the translational movement of the grating occurs at a relative position between the self-image and the plurality of gratings, there is a problem that the waveform of the acquired intensity change changes and therefore, the quality of the generated phase-contrast image deteriorates. Further, there is a need to improve phase sensitivity of a phase-contrast image, and further miniaturization of a period (pitch) of a grating is being progressed. When a period (pitch) of a grating is further miniaturized, a change in a waveform of an intensity change (deterioration of image quality) due to a positional deviation other than a positional deviation of a grating becomes more remarkable at a relative position between a self-image and a plurality of gratings.

The present invention has been made to solve the above-mentioned problems, and an object of the present invention is to provide an X-ray phase image capturing system capable of suppressing deterioration of image quality of an acquired phase-contrast image even in cases where a positional deviation other than a positional deviation due to a translational movement of a grating occurred at a relative position between a self-image and a plurality of gratings.

Means for Solving the Problem

In order to achieve the above object, an X-ray phase image capturing system according to one aspect of the present invention includes:
an X-ray source;
a plurality of gratings including a first grating to be irradiated with X-rays from the X-ray source and a second grating to be irradiated with the X-rays transmitted through the first grating;
a detector configured to detect the X-rays emitted from the X-ray source;
a moving mechanism configured to move at least one of the plurality of gratings;
an image processing unit configured to generate a phase-contrast image from an X-ray image set including a plurality of X-ray images detected by the detector,
wherein the image processing unit is configured to:
extract a plurality of feature quantities including at least one of an amplitude, average pixel value intensity, and a phase from a plurality of X-ray images sets acquired by performing fringe scanning a plurality of times in a short time; and
generate the phase-contrast image based on the plurality of feature quantities extracted.
Note that the X-ray image set denotes a set of a plurality of X-ray images acquired by single fringe scanning.

As described above, the X-ray phase image capturing system according to one aspect of the present invention is configured to generate a phase-contrast image based on feature quantities extracted from a plurality of X-ray image sets acquired by performing fringe scanning a plurality of times in a short time. Here, heat generation from the X-ray source and/or heat from the outside may cause thermal deformations of the moving mechanism. When the moving mechanism caused thermal deformations, the relative position between the gratings of the plurality of gratings changes. Since thermal deformations due to heat generation from an X-ray source and/or heat from the outside occur even during imaging, a relative position between gratings of a plurality of gratings is constantly changing. In addition, heat generation from an X-ray source and/or heat from the outside may cause thermal deformations of a grating. When a grating is thermally deformed, the period of the grating fluctuates. Variations in the period of the grating are also constantly occurring during the imaging. In addition, when X-rays are being emitted, the focal point of the X-ray source may move. When the focal point of the X-ray source moves, the self-image of the grating moves. Movements of the self-image of the grating are always being occurred during the imaging. That is, during the imaging, not only translational movements of the fringe scanning of the grating but also movements of the grating due to thermal fluctuations, movements of the period of the grating, and movements of the focal point of the X-ray source occur. Therefore, by configuring such that fringe scanning is performed a plurality of times in a short time as described above, it is possible to shorten the scanning time per imaging while translating the grating by one period of the grating, and therefore, it is possible to suppress the change in the relative position between the self-image and the grating that occurs during the fringe scanning. As a result, it is possible to suppress the change in the waveform of the acquired intensity change, which in turn can suppress deterioration of image quality of a generated phase-contrast image.

In the X-ray phase image capturing system according to the aforementioned one aspect of the present invention, preferably, the image processing unit is configured to generate the phase-contrast image based on the plurality of feature quantities extracted from the X-ray image set acquired by performing fringe scanning a plurality of times in a short time within a range in which an imaging condition change due to heat between the plurality of X-ray images does not substantially occur.

With such a configuration, the fringe scanning can be performed within a time range in which the imaging condition change due to heat between the plurality of X-ray images does not substantially occur. As a result, it is possible to suppress image quality deterioration of the phase-contrast image caused by the imaging condition changes due to heat. Note that in this specification, the term "imaging condition" refers to a relative position between a self-image and a grating, and the term "imaging condition change" refers to a positional deviation of a relative position between a self-image and a grating other than a positional deviation of the relative position between the self-image and the grating caused by the translational movement of the grating.

In the X-ray phase image capturing system according to the aforementioned one aspect of the present invention, preferably, the image processing unit is configured to generate the phase-contrast image based on the plurality of feature quantities extracted from the X-ray image set acquired by performing fringe scanning a plurality of times in a short time of 100 seconds or less. With such a configuration, since an X-ray image set is acquired in a short time of 100 seconds or less, it is possible to minimize the effect of the imaging condition change caused by the heat at the time of performing fringe scanning. As a result, it is possible to further suppress the change in the waveform of the acquired intensity change, which in turn can further suppress deterioration of the image quality of the acquired phase-contrast image.

In the X-ray phase image capturing system according to the aforementioned one aspect of the present invention, preferably, the image processing unit is configured to:

acquire a plurality of first feature quantities from a plurality of X-ray image sets acquired by performing fringe scanning a plurality of times in a short time without arranging a subject;

acquire a plurality of second feature quantities from a plurality of X-ray image sets acquired by performing fringe scanning a plurality of times in a short time while arranging a subject; and generate the phase-contrast image using at least one of the plurality of first feature quantities and at least one of the plurality of second feature quantities.

With this configuration, since the fringe scanning is performed in a short time, it is possible to acquire the first feature quantities and the second feature quantities acquired in a state in which imaging condition changes due to the heat generated during the X-ray image set acquisition are affected as free as possible. As a result, the first feature quantities and the second feature quantities can be made as less susceptible to imaging condition changes caused by the heat generated during the X-ray image set acquisition, so that deterioration of the image quality of the generated phase-contrast image can be further suppressed.

In this case, preferably, the image processing unit is configured to acquire one piece of feature quantity data from the plurality of first feature quantities and generate the phase-contrast image using the one piece of feature quantity data and the plurality of second feature quantities. With this configuration, since the feature quantity data is acquired from the plurality of first feature quantities each having a short exposure time (charge accumulation time) since the imaging is performed in a short time, it is possible to provide a feature quantity contrast stronger than that of each of the plurality of first feature quantities. Thus, a phase-contrast image can be generated using the feature quantity data contrasted more than each of the plurality of first feature quantities and the second feature quantities. As a result, it becomes possible to use the feature quantity data sharper in the feature quantity contrast than each of the plurality of first feature quantities captured in a short time, so that the image quality of the generated phase-contrast image can be improved.

In the configuration in which the phase-contrast image is generated using the one piece of feature quantity data and the plurality of second feature quantities, preferably, the image processing unit is configured to acquire the feature quantity data by adding or averaging the plurality of first feature quantities. With this configuration, it is possible to easily acquire the feature quantity data in which the contrast of the feature quantity is sharper because the quantum noise is smaller than each of the plurality of first feature quantities from the plurality of first feature quantities acquired in a short time.

In the configuration in which the phase-contrast image is generated using the one piece of feature quantity data and the plurality of second feature quantities, preferably, the image processing unit is configured to generate a phase-contrast image based on each of the plurality of second feature quantities and the feature quantity data. By configuring as described above, the phase-contrast image can be generated using the feature quantity data and each of the plurality of second feature quantities. As a result, for example, the image quality of the phase-contrast image generated from each of the plurality of second feature quantities can be improved as compared with the case in which the phase-contrast image is generated using the first feature quantity and each of the plurality of second feature quantities.

In the configuration in which the phase-contrast image is generated using the one piece of feature quantity data and the plurality of second feature quantities, preferably, the image processing unit is configured to add or average the phase-contrast images generated based on each of the plurality of second feature quantities and the feature quantity data. By configuring as described above, one phase-contrast image can be generated from a plurality of phase-contrast images generated based on the plurality of second feature quantities captured in a short time. As a result, for example, even in cases where imaging is performed with a long exposure time, fringe scanning can be performed a plurality of times in a short time as compared with a phase-contrast image captured by single fringe scanning, so it is possible to suppress accumulation of the effects of imaging condition changes caused by heat.

In the X-ray phase image capturing system according to one aspect of the present invention, preferably, the image processing unit is configured to perform extraction and calibration processing of the feature quantities from the X-ray image set in fringe scanning and acquisition of the X-ray image set in subsequent fringe scanning in parallel. By configuring as described above, since the extraction and calibration processing of the feature quantities from the X-ray image set and the acquisition of the X-ray image set in the subsequent fringe scanning can be performed in parallel, the production efficiency of the phase-contrast image can be improved compared with the case in which the extraction and calibration processing of the feature quantities and the generation of the phase-contrast image are performed every time the X-ray image set is acquired.

In this case, preferably, the phase-contrast image includes a phase differential image and the image processing unit is configured to perform, as the calibration processing, unwrap processing for continuing phase discontinuous points caused by phase reflection on the phase differential image. Note that phase discontinuous points are likely to occur at, e.g., a boundary between a subject and the background. Therefore, by configuring as described above, it is possible to eliminate the phase discontinuous point caused by phase reflection. As a result, even in cases where the position where a subject is reflected differs in respective X-ray images, it is possible to suppress phase discontinuous points from being synthesized, which in turn can suppress deterioration of the image quality of the generated phase differential image.

In the configuration in which the calibration processing of the X-ray image set is performed, preferably, the image processing unit is configured to perform, as the calibration processing, a brightness calibration for calibrating a change in the X-ray image detected by the detector including at least a change in a dose of the X-rays irradiated from the X-ray source. By configuring as described above, it is possible to calibrate artifacts caused by a change in an X-ray image caused by an imaging device such as a detector due to a short imaging time. As a result, even in cases where one phase-contrast image is generated from a plurality of phase-contrast images, it is possible to calibrate artifacts caused by an imaging device such as a detector generated in each phase-contrast image due to the short imaging time, so that the deterioration of the image quality of the phase-contrast image due to the accumulation of artifacts caused by the change in the X-ray image caused by the imaging device such as a detector can be suppressed.

In the X-ray phase image capturing system according to the one aspect of the present invention, preferably, the X-ray phase image capturing system further includes a control unit configured to control a grating movement in the moving mechanism, and the control unit is configured to determine a time for performing fringe scanning based on a period of the grating moved by the moving mechanism. By configuring as described above, for example, in a case where a period of a grating to be translated is 10 µm, it is possible to perform fringe scanning at an appropriate time based on the period of the grating, such as a short scanning time of 10 seconds. As a result, it becomes possible to perform the fringe scanning within a time range in which influences due to the positional deviation other than positional deviations due to the translational movement of the grating can be sufficiently suppressed at a relative position between the self-image and the plurality of gratings and it is possible to secure the exposure time as much as possible, so that deterioration of the image quality can be further reduced.

In the X-ray phase image capturing system according to the one aspect of the present invention, preferably, the control unit is configured to acquire a moving speed of a focal point of the X-ray source based on a position of a position reference portion reflected in each of X-ray images and determine a time of performing the fringe scanning based on the moving speed of the acquired focal point of the X-ray source. By configuring as described above, the movement of the focal point of the X-ray source can be detected based on the position of the position reference portion reflected in the X-ray image. As a result, even in cases where the focal point of the X-ray source has moved, it becomes possible to perform fringe scanning within a time range in which the effect of the movement of the focal point of the X-ray source can be sufficiently suppressed and it becomes possible to secure the exposure time as much as possible, so that it is possible to suppress deterioration of the image quality caused by the movement of the self-image caused by the movement of the focal point of the X-ray source.

In the X-ray phase image capturing system according to the one aspect of the present invention, preferably, the X-ray phase image capturing system further includes a rotating mechanism configured to relatively rotate an imaging system composed of an X-ray source, a detector, and a plurality of gratings and a subject, wherein the image processing unit is configured to generate a three-dimensional phase-contrast image from a plurality of phase-contrast images captured at a plurality of rotation angles while relatively rotating a subject and the imaging system. By configuring as described above, it is possible to generate a three-dimensional phase-contrast image by using respective phase-contrast images in which deterioration of the image quality caused by the change of the imaging condition due to heat is suppressed. As a result, it is possible to effectively suppress deterioration of the image quality of the three-dimensional phase-contrast image to be generated even in the case of acquiring the three-dimensional phase-contrast image in which the imaging time becomes long and the effect of the imaging condition change due to heat is likely to occur.

In the X-ray phase image capturing system according to one aspect of the present invention, preferably, the plurality of gratings further includes a third grating arranged between the X-ray source and the first grating. By configuring as described above, the coherence of the X-rays emitted from the X-ray source by the third grating can be enhanced. As a result, since it becomes possible to form a self-image of the first grating without depending on the focal diameter of the X-ray source, the degree of flexibility in selecting the X-ray source can be improved.

Effects of the Invention

According to the present invention, as described above, it is possible to provide an X-ray phase image capturing system capable of suppressing deterioration of image quality of an acquired phase-contrast image even in cases where a positional deviation other than a positional deviation caused by a translational movement of a grating occurs at a relative position between a self-image and a plurality of gratings.

EMBODIMENTS FOR CARRYING OUT THE INVENTION

Hereinafter, embodiments in which the present invention is embodied will be described with reference to the attached drawings.

First Embodiment

Referring to FIG. 1 to FIG. 6, a configuration of an X-ray phase image capturing system 100 according to a first embodiment of the present invention will be described.

(Configuration of X-Ray Phase Image Capturing System)

First, a configuration of an X-ray phase image capturing system 100 according to a first embodiment of the present invention will be described with reference to FIG. 1.

Figure 1:
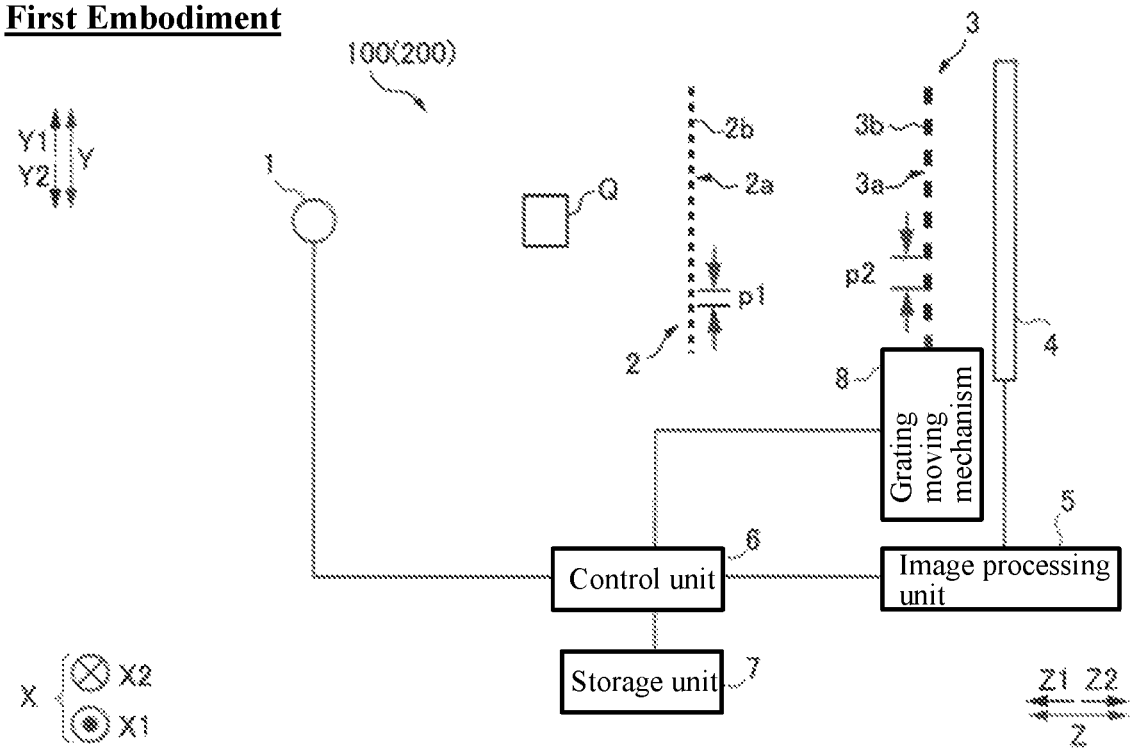
FIG. 1 is a schematic diagram of an X-ray phase image capturing system according to a first embodiment of the present invention as viewed from an X-direction.

FIG. 1 is a view of the X-ray phase image capturing system 100 as viewed from the X-direction. As shown in FIG. 1, the X-ray phase image capturing system 100 is provided with an X-ray source 1, a first grating 2, a second grating 3, a detector 4, an image processing unit 5, a control unit 6, a storage unit 7, and a moving mechanism 8. Note that in this specification, the direction from the X-ray source 1 toward the first grating 2 is referred to as a Z2-direction, and the opposite direction thereof is referred to as a Z2-direction. The left-right direction in a plane orthogonal to the Z-direction is defined as an X-direction, the direction toward the back side of the paper is defined as an X2-direction, and the direction toward the front side of the paper is defined as an X1-direction. The up-down direction in a plane orthogonal to the Z-direction is defined as a Y-direction, the upward direction is defined as a Y1-direction, and the downward direction is defined as a Y2-direction.

The X-ray source 1 is configured to emit X-rays when a high voltage is applied based on the signal from the control unit 6 and emit the generated X-rays toward to the detector 4 (Z-direction).

The first grating 2 has a plurality of slits 2a and X-ray phase change portions 2b arranged at a predetermined period (pitch) p1 in a certain direction. The slit 2a and the X-ray phase change portion 2b are each formed so as to extend linearly. The slit 2a and the X-ray phase change portion 2b are each formed so as to extend in parallel with each other. In the example shown in FIG. 1, the respective slits 2a and X-ray phase change portions 2b are arranged at a predetermined period (pitch) p1 in the Y-direction and are formed to extend in the X-direction. The first grating 2 is a so-called phase grating.

The first grating 2 is arranged between the X-ray source 1 and the second grating 3, and is irradiated with the X-rays from the X-ray source 1. The first grating 2 is provided to form a self-image (not shown) of the first grating 2 by a Talbot effect. When coherent X-rays pass through a grating in which slits are formed, an image of the grating (self-image) is formed at a predetermined distance (Talbot distance) from the grating. This is called a Talbot effect.

The second grating 3 is provided with a plurality of X-ray transmission portions 3a and X-ray absorption portions 3b arranged at a predetermined period (pitch) p2 in a certain direction. The X-ray transmission portion 3a and the X-ray absorption portion 3b are each formed so as to extend linearly. The X-ray transmission portion 3a and the X-ray absorption portion 3b are each formed so as to extend in parallel with each other. In the example shown in FIG. 1, the X-ray transmission portion 3a and the X-ray absorption portion 3b are each arranged at a predetermined period (pitch) p2 in the Y-direction, and are formed to extend in the X-direction. The second grating 3 is a so-called absorption grating. The first grating 2 has a function of changing the phase of the X-rays by a difference in the refractive index between the X-ray phase change portion 2b and the slit 2a. The second grating 3 has a function of shielding a part of the X-rays by the X-ray absorption portions 3b.

The second grating 3 is arranged between the first grating 2 and the detector 4, and is irradiated with the X-rays that have passed through the first grating 2. In addition, the second grating 3 is arranged at a position away from the first grating 2 by the Talbot distance. The second grating 3 interferes with the self-image of the first grating 2 to form a Moire fringe (not shown) on the sensing surface of the detector 4.

The detector 4 is configured to detect X-rays, convert the detected X-rays into an electric signal, and read the converted electric signal as an image signal. The detector 4 is, for example, an FPD (Flat Panel Detector). The detector 4 is composed of a plurality of conversion elements (not shown) and a plurality of pixel electrodes (not shown) arranged on the conversion elements. The plurality of conversion elements and pixel electrodes are arranged in an array in the X-direction and Y-direction at a predetermined period (pixel pitch). The detector 4 is also configured to output the acquired image signal to the image processing unit 5.

The image processing unit 5 is configured to generate an X-ray image set R (see FIG. 3) including a plurality of X-ray images 11 (see FIG. 3) based on the image signal output from the detector 4. The image processing unit 5 is configured to acquire first feature quantities 12 (see FIG. 3), feature quantity data 13 (see FIG. 3), and second feature quantities 14 (see FIG. 4) based on the generated X-ray image set R. The image processing unit 5 is also configured to generate phase-contrast images 15 (see FIG. 4) based on the feature quantity data 13 and the second feature quantities 14. The processing in which the image processing unit 5 acquires the first feature quantities 12, the feature quantity data 13, the second feature quantities 14 and the processing in which the image processing unit 5 generates the phase-contrast images 15 will be described later. The image processing unit 5 includes processors, such as, e.g., a GPU (Graphics Processing Unit) and an FPGA (Field-Programmable Gate Array) configured for imaging processing.

The control unit 6 is configured to move the second grating 3 stepwise within the grating plane in a direction (X-direction) perpendicular to the grating direction (Y-direction) via the moving mechanism 8. The control unit 6 is configured to determine a time for moving the second grating 3 stepwise in a direction (X-direction) perpendicular to the grating direction (Y-direction) based on the period p2 of the second grating 3 and the movement of the focal point of the X-ray source 1. The detailed configuration for determining the time that the control unit 6 moves the second grating 3 stepwise will be described later. Further, the control unit 6 includes processors, such as, e.g., a CPU (Central Processing Unit).

The storage unit 7 is configured to store the X-ray image set R, the first feature quantities 12, the feature quantity data 13, the second feature quantities 14, and the phase-contrast images 15 generated by the image processing unit 5. The storage unit 7 includes, for example, an HDD (hard disk drive) and a nonvolatile memory.

The moving mechanism 8 is configured to move the second grating 3 stepwise in a direction (X-direction) perpendicular to the grating direction (Y-direction) in the grating plane (XY-plane) based on the signal from the control unit 6. More specifically, the moving mechanism 8 moves the second grating 3 stepwise by p2/M obtained by dividing the period p2 of the second grating 3 by M. Note that M is a positive integer and, in the first embodiment, M=4, for example. The moving mechanism 8 includes, for example, a stepping motor or a piezo actuator.

(Relationship between Scanning Time Difference and Waveform Intensity Change)

Next, referring to FIG. 2, the relationship between the difference of the scanning time and the waveform 10 of the intensity change will be described. The scanning time refers to the time duration for moving the second grating 3 stepwise M times by the moving mechanism 8.

Figure 2:
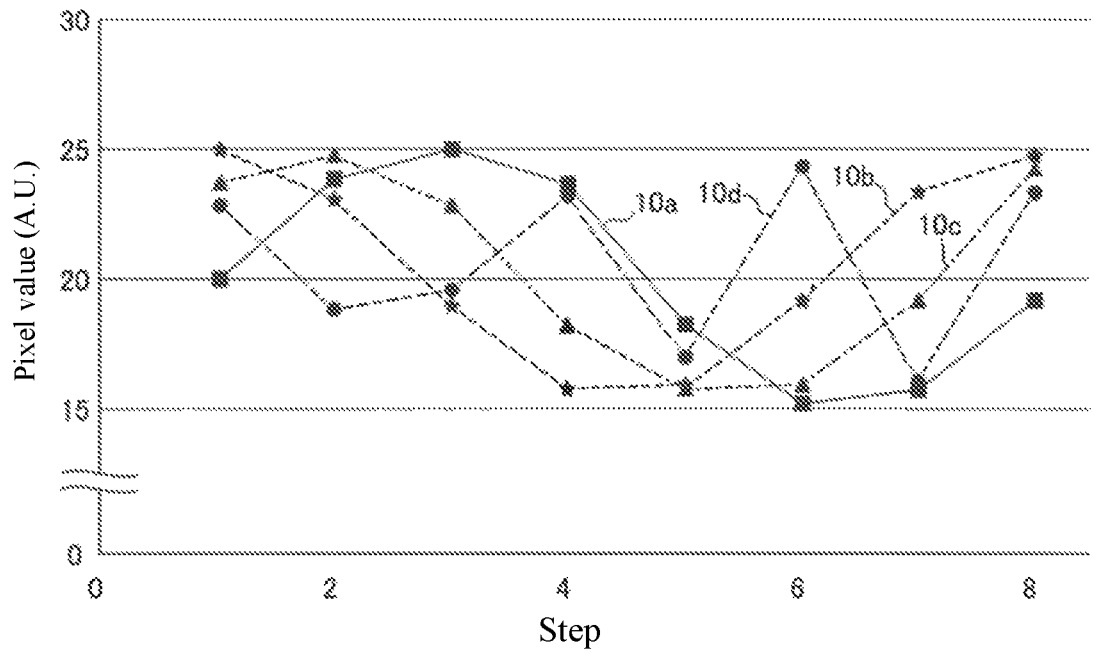
FIG. 2 is a schematic diagram for explaining a relationship between a scanning time and a waveform change of an intensity change of a pixel value in a pixel.

FIG. 2 is a schematic diagram showing the difference in the waveform 10 of the intensity change in a case where the time for translating the second grating 3 by the moving mechanism 8 is changed when the image processing unit 5 generates the phase-contrast image 15 by a fringe scanning method. In the case shown in FIG. 2, in order to make the waveform 10 of the intensity change easy to understand, the waveform 10 of the intensity change in a case where the second grating 3 is translated by eight steps, wherein M is eight (M=8). Here, it is assumed that the relative positional relation between the first grating 2 and the second grating 3 varies at a constant rate due to external factors, such as, e.g., thermal fluctuations, in addition to the translational movements of the fringe scanning.

The variation due to an external factor includes, for example, a variation due to the thermal deformation of the moving mechanism 8 caused by the heat generation from the X-ray source 1 and/or heat from the outside. In cases where the moving mechanism 8 is thermally deformed, the relative position between the gratings of the plurality of gratings changes. Since the heat fluctuations due to the heat generation from the X-ray source 1 and/or the heat from the outside occur during the imaging, the relative positions between gratings of the plurality of gratings constantly change. Further, there is a case in which the second grating 3 is thermally deformed by the heat generation from the X-ray source 1 and/or the heat from the outside. When the second grating 3 is thermally deformed, the period p2 of the second grating 3 fluctuates. Variations in the period p2 of the second grating 3 also constantly occur during the imaging. Further, when X-rays are being emitted, there is a case that the focal point of the X-ray source 1 moves. When the focal point of the X-ray source 1 moves, the self-image of the first grating 2 moves. Movements of the self-image of the first grating 2 are constantly occurring during the imaging. That is, during the imaging, not only translational movements of the gratings but also the movement of the second grating 3 due to the thermal fluctuation, the change of the period p2 of the second grating 3, and the movement of the focal point of the X-ray source 1 are occurring. These cause a positional deviation in the relative position between the self-image of the first grating 2 and the plurality of gratings other than the positional deviation due to the translational movements of the second grating 3. Therefore, as shown in FIG. 2, when the duration of one fringe scanning becomes longer, a positional deviation other than a positional deviation due to the translational movements of the second grating 3 occurs in the relative position between the self-image of the first grating 2 and the plurality of gratings due to the effect of the thermal fluctuation, and therefore, the waveform 10 of the acquired intensity change changes.

The waveform 10*a* of the intensity change (solid line graph), the waveform 10*b* of the intensity change (dashed line graph), and the waveform 10*c* of the intensity change (dashed line graph) each are a waveform 10 of intensity change when single fringe scanning is performed in a short time. The scanning time of the waveforms 10*a* to 10*c* of the intensity change is, for example, 10 seconds. The waveform 10*d* of the intensity change (two-dot chain line graph) is a waveform 10 of the intensity change when single fringe scanning is performed in three times scanning time of the waveforms 10*a* to 10*c* of the intensity change. The waveforms 10*a* to 10*c* of the intensity change differs in their respective initial phases but have shapes that can be generally regarded as a sine wave. On the other hand, it is understood that the waveform 10*d* of the intensity change has a waveform in which the waveform is distorted as the step progresses and cannot be regarded as a sine wave. In a fringe scanning method, since the phase-contrast image 15 is generated by assuming that the waveform 10 of the acquired intensity change is a sine wave, if the waveform 10 of the acquired intensity change is distorted, the image quality of the generated phase-contrast image 15 is deteriorated. Therefore, in the first embodiment, the X-ray phase image capturing system 100 is configured so as to be hardly affected by thermal fluctuations as much as possible and to be able to suppress a change in the waveform 10 of the acquired intensity change. Hereinafter, the detailed configuration capable of suppressing the change in the waveform 10 of the acquired intensity change will be described.

(Configuration of Image Processing Unit)

Next, referring to FIG. 3 to FIG. 5, the processing will be described in which the image processing unit 5 according to the first embodiment generates a phase-contrast image 15.

In the first embodiment, the image processing unit 5 is configured to extract feature quantities 12 (and feature quantities 14) containing at least one of an amplitude, an average pixel value intensity, and a phase from a plurality of X-ray image sets R acquired by performing fringe scanning a plurality of times in a short time and generate a phase-contrast image 15 based on the plurality of feature quantities 12 (and feature quantities 14) extracted, respectively. Specifically, the image processing unit 5 is configured to generate a phase-contrast image 15 based on the plurality of feature quantities 12 (and feature quantities 14) extracted from the X-ray image set R acquired by performing a plurality of fringe scanning in a short time within a range in which the imaging condition does not substantially change due to heat between a plurality of X-ray images 11. In the first embodiment, the image processing unit 5 is configured to generate a phase-contrast image 15 based on the plurality of feature quantities 12 (and feature quantities 14) extracted from the X-ray image set R acquired by performing the fringe scanning several times in a short time of 100 seconds or less, as the short time within which the imaging condition does not substantially change due to heat.

Note that the first feature quantities 12 include a feature quantity 12*a* for an absorption image acquired based on the average pixel value intensity of the waveform 10 of the intensity change acquired by performing the imaging without arranging a subject Q. The first feature quantities 12 include a feature quantity 12*b* for a phase differential image acquired based on the phase of the waveform 10 of the intensity change acquired by performing the imaging without arranging a subject Q. The first feature quantities 12 include an amplitude of the waveform 10 of the intensity change captured by performing the imaging in a state in which a subject Q is arranged and the feature quantity 12*c* for a dark-field image acquired based on the average pixel value intensity. The feature quantity data 13 include one piece of feature quantity data 13*a* for an absorption image acquired by adding and averaging a plurality of first feature quantities 12, one piece of feature quantity data 13*b* for a phase differential image, and one piece of feature quantity data 13*c* for a dark-field image. The second feature quantities 14 include a feature quantity 14*a* for an absorption image acquired based on the average pixel value intensity of the waveform 10 of the intensity change acquired by performing the imaging in a state in which a subject Q is arranged. Further, the second feature quantities 14 include a feature quantity 14*b* for a phase differential image acquired based on the phase of the waveform 10 of the intensity change acquired by performing the imaging in a state in which a subject Q is arranged. The first feature quantities 12 include a feature quantity 14*c* for a dark-field image acquired based on the amplitude of the waveform 10 of the intensity change acquired by performing the imaging in a state in which a subject Q is arranged and the average pixel value intensity.

In the first embodiment, the image processing unit 5 is configured to acquire a plurality of first feature quantities 12 from a plurality of first X-ray image sets Ra captured by performing fringe scanning a plurality of times in a short time without arranging a subject Q, acquire a plurality of second feature quantities 14 from a plurality of second X-ray image sets Rb acquired by performing fringe scanning a plurality of times in a short time by arranging a subject Q, and generate a phase-contrast image 15 using at least one of the plurality of first feature quantities 12 and at least one of the plurality of second feature quantities 14.

Here, in the first embodiment, the image processing unit 5 is configured to acquire first feature quantities 12 based on an X-ray image set R captured by single fringe scanning in a short time of 100 seconds or less. Therefore, the exposure time per one scanning (charge accumulation time) is shortened. Therefore, the contrast of each of the plurality of first feature quantities 12 is not so high. Therefore, in the first embodiment, the image processing unit 5 is configured to acquire one piece of feature quantity data 13 from a plurality of first feature quantities 12 and generate a phase-contrast image 15 using one piece of feature quantity data 13 and a plurality of second feature quantities 14.

(Acquisition of First Feature Quantities and Feature Quantity Data)

Figure 3:
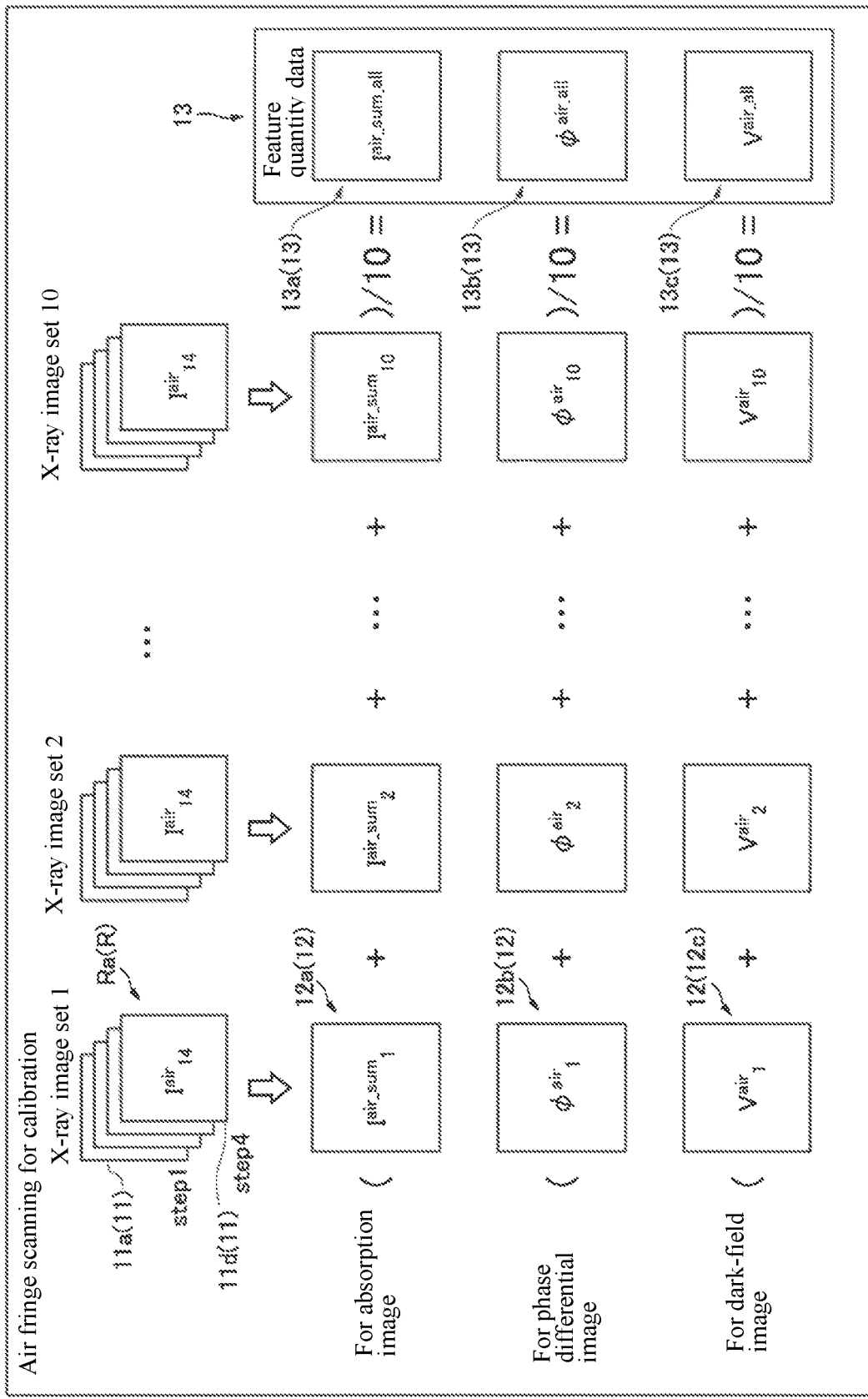
FIG. 3 is a schematic diagram for explaining the processing in which an image processing unit according to a first embodiment of the present invention acquires feature quantity data.

FIG. 3 is a schematic diagram for explaining the processing in which the image processing unit 5 according to the first embodiment acquires first feature quantities 12 and feature quantity data 13.

In the first embodiment, the image processing unit 5 is configured to acquire, as first feature quantities 12, a feature quantity 12*a* for an absorption image, a feature quantity 12*b* for a phase differential image, and a feature quantity 12*c* for a dark-field image. Specifically, the image processing unit 5 is configured to acquire a plurality of first X-ray image sets Ra each including M pieces (four pieces) of X-ray images 11 (X-ray images 11*a* to 11*d*) captured while moving the second grating 3 M times (four times) stepwise in a state in which no subject Q is arranged.

A pixel value of a pixel of the X-ray image 11 captured without arranging a subject Q is defined as $I^{air}_{jk}(x, y)$, and the following $S^{air}_j(x, y)$ is defined.

$$S^{air}_j(x, y) = \sum_{k=1}^{M} I^{air}_{jk}(x, y)\exp\left(-\frac{2i\pi k}{M}\right) \quad (1)$$

where, "M" is the number of times to translate the second grating 3. "k" is a number of each step when translating the second grating 3 and is a positive integer from 1 to M. "j" is a positive integer from 1 to the set number (number of pieces) of the X-ray image set R. In the first embodiment, for example, "j" is a positive number of 1 to 10. "x" and "y" are the x coordinate x and y coordinate of each pixel in the X-ray image 11.

The image processing unit 5 is configured to acquire, as the first feature quantities 12, a feature quantity 12a for an absorption image, a feature quantity 12b for a phase differential image, and a feature quantity 12c for a dark-field image from the first X-ray image set Ra based on the following expressions (2) to (4).

$$I^{air\_sum}_j(x, y) = \sum_{k=1}^{M} I^{air}_{jk}(x, y) \quad (2)$$

$$\phi^{air}_j(x, y) = \arg[S^{air}_j(x, y)] \quad (3)$$

$$V^{air}_j(x, y) = \frac{2|S^{air}_j(x, y)|}{I^{air\_sum}(x, y)} \quad (4)$$

where $I^{air\_sum}_j(x, y)$ is a feature quantity 12a for an absorption image. Further, $\phi^{air}_j(x, y)$ is a feature quantity 12b for a phase differential image. Further, $V^{air}_j(x, y)$ is a feature quantity 12c for a dark-field image.

In the example shown in FIG. 3, the image processing unit 5 is configured to acquire a plurality of sets (10 sets from j=1 to 10) of the first X-ray image sets Ra and acquire a feature quantity 12 from each of them. In the first embodiment, the image processing unit 5 is configured to acquire one piece of feature quantity data 13 from ten sets of first X-ray image sets Ra. Specifically, as shown in the following expressions (5) to (7), the image processing unit 5 is configured to acquire the feature quantity data 13 by adding and averaging the plurality of first feature quantities 12.

$$I^{air\_sum\_all}(x, y) = \frac{1}{N}\sum_{j=1}^{N} I^{air\_sum}_j(x, y) \quad (5)$$

$$\phi^{air\_all}(x, y) = \frac{1}{N}\sum_{j=1}^{N} \phi^{air}_j(x, y) \quad (6)$$

$$V^{air\_all}(x, y) = \frac{1}{N}\sum_{j=1}^{N} V^{air}_j(x, y) \quad (7)$$

(Acquisition of Second Feature Quantity and Generation Processing of Phase-Contrast Image)

Next, referring to FIG. 4 and FIG. 5, the configuration in which the image processing unit 5 according to the first embodiment acquires the second feature quantities 14 and the configuration in which the image processing unit 5 generates the phase-contrast image 15 will be described.

Figure 4:
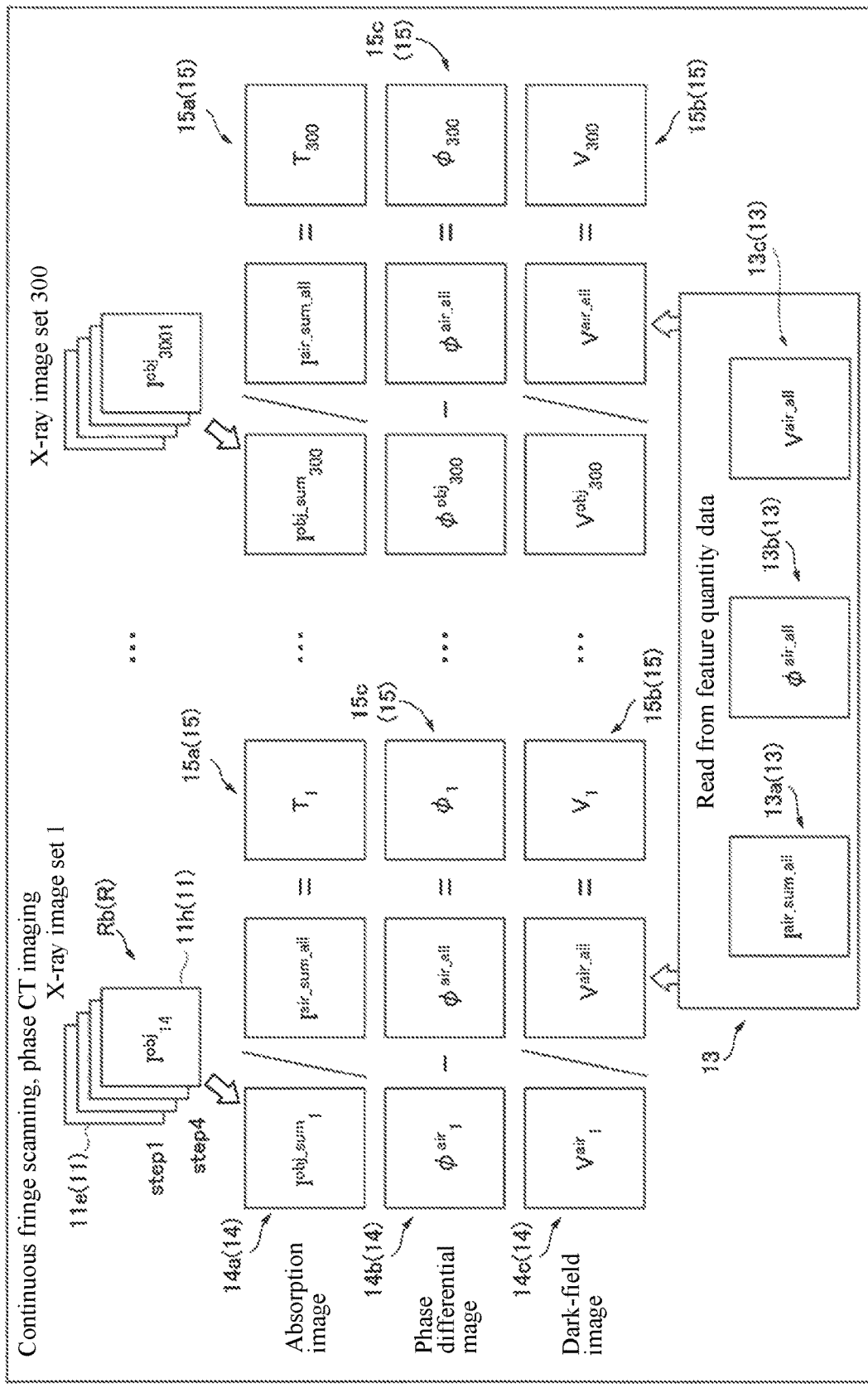
FIG. 4 is a schematic diagram for explaining the processing in which the image processing unit according to the first embodiment of the present invention generates a phase-contrast image.

As shown in FIG. 4, in the first embodiment, the image processing unit 5 is configured to acquire second feature quantities 14 from second X-ray image sets Rb including M pieces (4 pieces) of X-ray images 11 (X-ray images 11e to 11h) captured while moving the second grating 3 M times (4 times) stepwise in a state in which the subject Q is arranged.

The pixel value of the pixel of the X-ray image 11 captured in a state in which a subject Q is arranged is $I^{obj}_{jk}(x, y)$, and the following $S^{obj}_j(x, y)$ is defined.

$$S^{obj}_j(x, y) = \sum_{k=1}^{M} I^{obj}_{jk}(x, y)\exp\left(-\frac{2i\pi k}{M}\right) \quad (8)$$

Further, the pixel value of the X-ray image 11 acquired by single fringe scanning in a state in which a subject Q is arranged can be represented by the following expression (9).

$$I^{obj\_sum}_j(x, y) = \sum_{k=1}^{M} I^{obj}_{jk}(x, y) \quad (9)$$

Further, the phase of the X-ray image acquired in a state in which a subject Q is arranged can be represented by the following expression (10).

$$\phi^{obj}_j(x,y)=\arg[S^{obj}_j(x,y)] \quad (10)$$

where, $\phi^{obj}_j(x, y)$ is a feature quantity 14b for a phase differential image.

Further, the visibility of the X-ray image acquired in a state in which a subject Q is arranged can be represented by the following expression (11).

$$V^{obj}_j(x, y) = \frac{2|S^{obj}_j(x, y)|}{I^{obj\_sum}_j(x, y)} \quad (11)$$

where, $V^{obj}_j(x, y)$ is a feature quantity 14c for a dark-field image.

The absorption image 15a, the phase differential image 15b, and the dark-field image 15c can be represented by the following expressions (12) to (14).

$$T_j(x, y) = \frac{I^{obj\_sum}_j(x, y)}{I^{air\_sum\_all}(x, y)} \quad (12)$$

$$\phi_j(x, y) = (\arg[S^{obj}_j(x, y)] - \phi^{air\_all}(x, y)) = \left(\arctan\left[\frac{S\_\sin^{obj}_j(x, y)}{S\_\cos^{obj}_j(x, y)}\right] - \phi^{air\_all}(x, y)\right) \quad (13)$$

$$D_j(x, y) = \frac{V^{obj}_j(x, y)}{V^{air\_all}(x, y)} \quad (14)$$

where $T_j(x, y)$ is a pixel value of each pixel of the absorption image 15a. Further, $\phi_j(x, y)$ is a pixel value of each pixel of the phase differential image 15b. Further, $D_j(x, y)$ is a pixel value of each pixel of the dark-field image 15c.

In the first embodiment, the image processing unit 5 is configured to generate a phase-contrast image 15 based on each of the plurality of second feature quantities 14 and the feature quantity data 13 by the expressions (12) to (14). In the example shown in FIG. 4, the image processing unit 5 is configured to acquire a plurality of sets (300 sets of j=1 to 300) of the second X-ray image sets Rb and acquire a second feature quantity 14 from each of them. In the first embodiment, the image processing unit 5 is configured to generate a plurality of phase-contrast images 15 using each of the second feature quantities 14 acquired from the plurality of second X-ray image sets Rb and the feature quantity data 13.

Specifically, the image processing unit 5 is configured to generate a plurality of absorption images 15a using the feature quantity data 13a for an absorption image acquired based on the expression (5), a plurality of feature quantities 14a for an absorption image acquired based on the expression (9), and the expression (12). Further, the image processing unit 5 is configured to generate a plurality of phase differential images 15b using the feature quantity data 13b for a phase differential image acquired based on the expression (6), a plurality of feature quantities 14b for a phase differential image acquired based on the expression (10), and the expression (13). The image processing unit 5 is configured to generate a plurality of dark-field images 15c using the feature quantity data 13c for a dark-field image acquired based on the expression (7), the plurality of feature quantities 14c for a dark-field image acquired based on the expression (11), and the expression (14).

Further, as described above, since the second X-ray image set Rb used for acquiring second feature quantities 4 is also captured by the short-time fringe scanning, the exposure time (charge accumulation time) is short. Accordingly, in the first embodiment, the image processing unit 5 is configured to add and average the phase-contrast images 15 generated based on each of the plurality of second feature quantities 14 and the feature quantity data 13. In the example shown in FIG. 4, the image processing unit 5 may generate one absorption image 15a, one phase differential image 15b, and one dark-field image 15c by adding or averaging the generated plurality (300 pieces) of absorption images 15a, phase differential images 15b, and dark-field images 15c, respectively.

Figure 5:
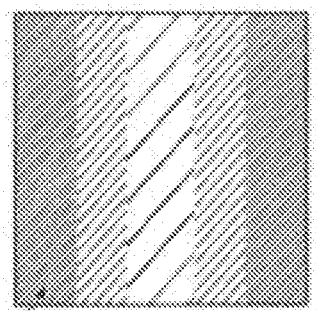
FIG. 5 is a schematic diagram including a schematic diagram (A) showing feature quantity data, a schematic diagram (B) showing second feature quantities, and a schematic diagram (C) showing phase-contrast images.
Figure 5:
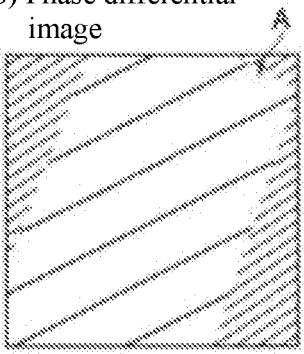
Figure 5:
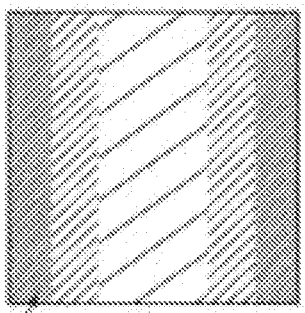
Figure 5:
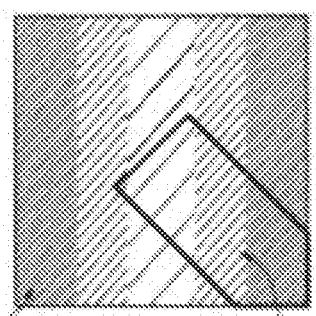
Figure 5:
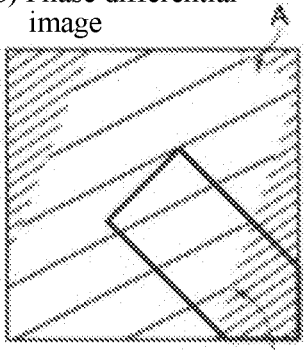
Figure 5:
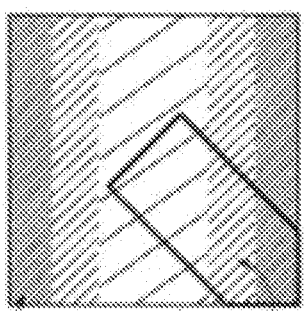
Figure 5:
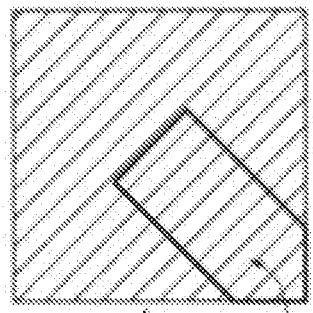
Figure 5:
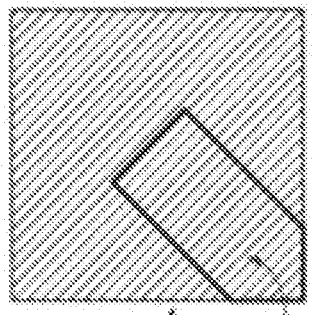
Figure 5:
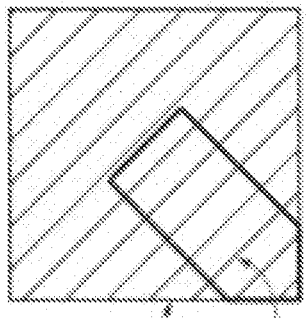

(A) of FIG. 5 is a schematic diagram of the feature quantity data 13 acquired by the image processing unit 5 according to the first embodiment. (B) of FIG. 5 is a schematic diagram of the second feature quantities 14 acquired by the image processing unit 5 according to the first embodiment. (C) of FIG. 5 is a schematic diagram of the phase-contrast images 15 generated by the image processing unit 5 according to the first embodiment.

As shown in (A) of FIG. 5 and (B) of FIG. 5, a gradation-like artifact A is generated in the background of the feature quantity data 13 and the second feature quantity 14. In the first embodiment, as shown in (C) of FIG. 5, the image processing unit 5 generates a phase-contrast image 15 using the feature quantity data 13 and the second feature quantity 14 in which the artifact A occurs, so it can be seen that the gradient artifact A in the background has been removed from the phase-contrast image 15 generated based on the feature quantity data 13 and the second feature quantity 14.

(Determination of Scanning Time)

Also, as described above, during the imaging, by the heat from the X-ray source 1 and/or the outside, in addition to the translational movement of the grating, movements of the second grating 3, variations of the period p2 of the second grating 3, and movements of the focal point of the X-ray source 1 are occurring. Therefore, in the first embodiment, the control unit 6 is configured to set the time of single fringe scanning to a short time so as not to be affected by thermal fluctuations as much as possible. In the first embodiment, the control unit 6 is configured to determine the scanning time such that, for example, if the period p2 of the second grating 3 is 10 m, the movement of the second grating 3 due to thermal fluctuations becomes 1 m or less. In the first embodiment, it is assumed that the moving speed of the second grating 3 due to thermal fluctuations is constant.

Also, in the first embodiment, the control unit 6 is configured to acquire the moving speed of the focal point of the X-ray source 1 based on the position of a position reference portion 16 (see FIG. 6) reflected in each of the X-ray images 11, and the control unit 6 is configured to determine the time for performing the fringe scanning based on the moving speed of the focal point of the X-ray source 1 acquired.

Figure 6:
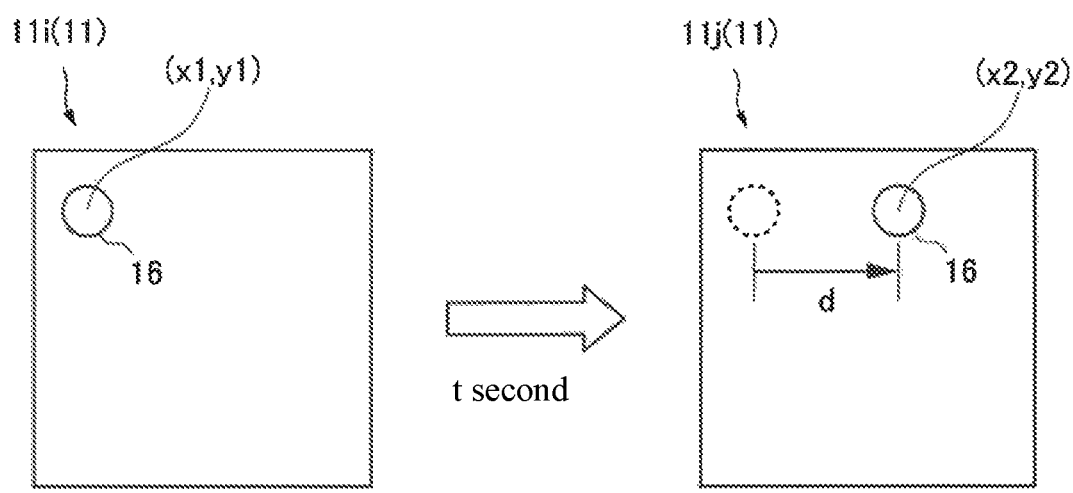
FIG. 6 is a schematic diagram for explaining the processing in which a control unit according to the first embodiment of the present invention acquires a moving speed of a focal point of an X-ray source.

FIG. 6 is a diagram for explaining the processing in which the control unit 6 acquires the moving speed of the focal point of the X-ray source 1. As shown in FIG. 6, the image processing unit 5 acquires the position (x1, y1) of the position reference portion 16 reflected in the X-ray image 11i. Thereafter, the image processing unit 5 acquires the position (x2, y2) of the position reference portion 16 reflected in the X-ray image 11j captured t seconds later. The image processing unit 5 is configured to acquire the moving distance d of the position reference portion 16 from the X-ray image 11i and the X-ray image 11j. Further, the control unit 6 is configured to acquire the moving speed of the position reference portion 16 by using the moving distance d of the acquired position reference portion 16 and the time t seconds between the image capturing of the X-ray image 11i and the image capturing of the X-ray image 11j.

Here, the position reference portion 16 is fixedly arranged between the X-ray source 1 and the first grating 2 or between the first grating 2 and the second grating 3. The position reference portion 16 is formed of an X-ray superabsorber having a high X-ray absorptivity. The X-ray superabsorber is, for example, a heavy metal. In the first embodiment, for example, a heavy metal, such as, e.g., tungsten, gold, and lead, is used as the position reference portion 16. Since the position reference portion 16 is fixedly arranged, in a case where the position of the position reference portion 16 in the X-ray image 11 has changed, it is considered that the movement of the focal point of the X-ray source 1 has occurred. Accordingly, in the first embodiment, the image processing unit 5 is configured to acquire the moving speed of the position reference portion 16 acquired based on the change in the position of the position reference portion 16 reflected in the plurality of X-ray images 11 as the moving speed of the focal point of the X-ray source 1.

In the first embodiment, the control unit 6 is configured to determine, for example, the scanning time of the second grating 3 in a short time of 10 seconds in cases where the moving speed of the focal point of the X-ray source 1 is 10 m/100 seconds and the period p2 of the second grating 3 is 10 m.

(Generation Processing of Phase-Contrast Image)

Next, referring to FIG. 7 to FIG. 11, the generation processing of the phase-contrast image 15 according to the first embodiment will be described.

Figure 7:
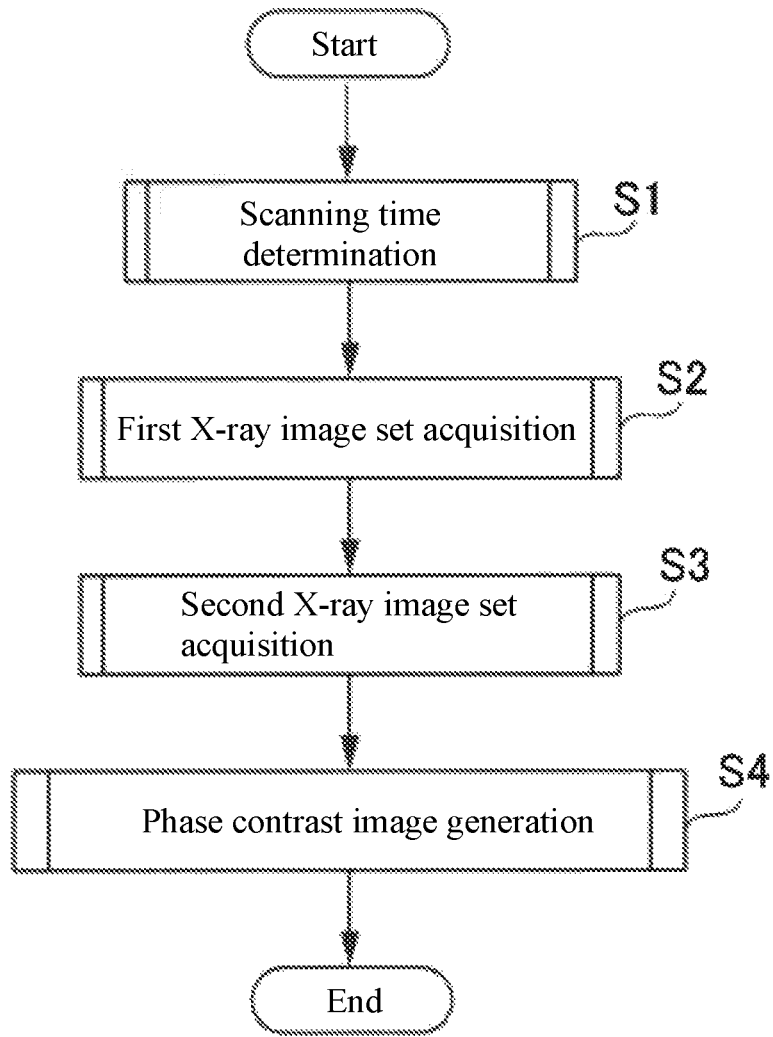
FIG. 7 is a flowchart for explaining phase-contrast image acquisition processing by the first embodiment of the present invention.
Figure 8:
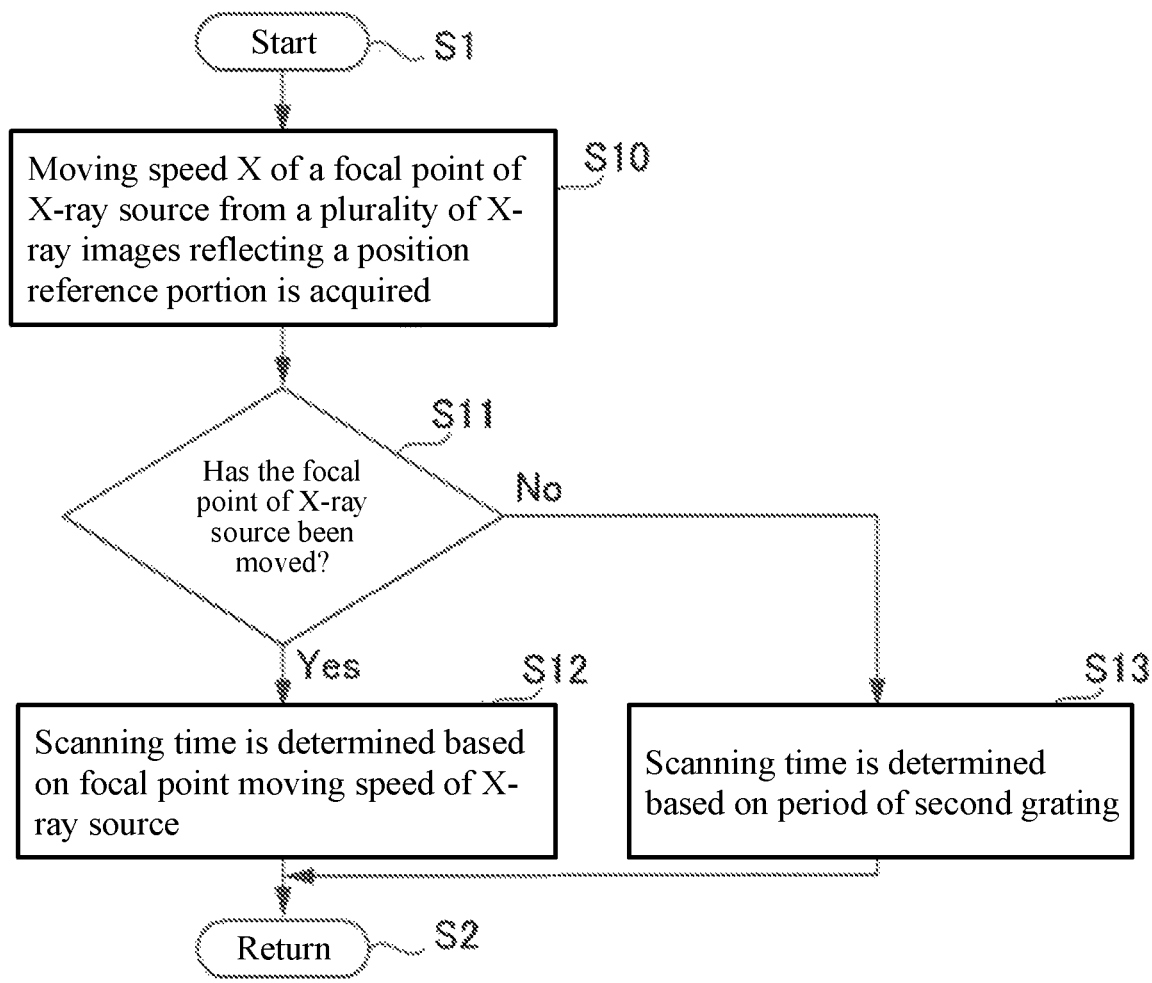
FIG. 8 is a schematic diagram for explaining scanning time determination processing by the first embodiment of the present invention.

As shown in FIG. 7, in Step S1, the control unit 6 determines the scanning time of the second grating 3 prior to acquiring the X-ray image set R. Next, in Step S2, the image processing unit 5 acquires the first X-ray image set Ra captured in a state in which no subject Q is arranged. Thereafter, processing proceeds to Step S3.

In Step S3, the image processing unit 5 acquires the second X-ray image set Rb acquired in a state in which a subject Q is arranged. Thereafter, in Step S4, the image processing unit 5 generates a phase-contrast image 15 and terminates the processing.

Next, referring to FIG. 8 to FIG. 11, the respective processing will be described in detail. First, referring to FIG. 8, the processing for determining the scanning time of the second grating 3 in Step S1 of FIG. 7 will be described.

In Step S10, the image processing unit 5 acquires a plurality of X-ray images 11 in which the position reference portion 16 is reflected. The control unit 6 then acquires the moving speed of the focal point of the X-ray source 1 from the plurality of X-ray images 11 in which the position reference portion 16 is reflected. Next, in Step S11, the control unit 6 determines whether or not the focal point of the X-ray source 1 is moving based on the acquired moving speed of the focal point of the X-ray source 1. If the focal point of the X-ray source 1 is moving, the processing proceeds to Step S12. If the focal point of the X-ray source 1 is not moving, the processing proceeds to Step S13.

In Step S12, the image processing unit 5 determines the scanning time of the second grating 3 based on the moving speed of the focal point of the X-ray source 1. Thereafter, the processing returns to Step S2.

Also in Step S13, the control unit 6 determines the time for performing the fringe scanning based on the period p2 of the second grating 3 moved by the moving mechanism 8. More specifically, for example, in a case where the period p2 of the second grating 3 is 10 μm, the fringe scanning time is determined so that the movement of the second grating 3 due to thermal fluctuations becomes 1 μm or less. Then, the processing returns to Step S2.

Figure 9:
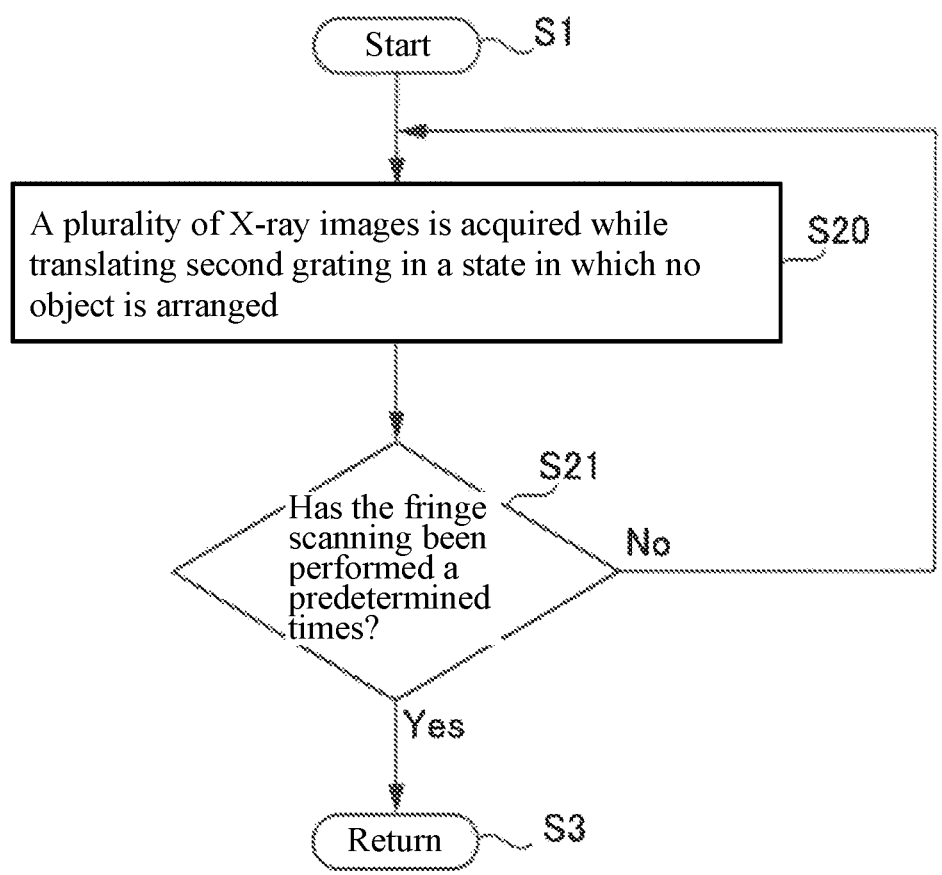
FIG. 9 is a schematic diagram for explaining first X-ray image set acquisition processing according to the first embodiment of the present invention.

Next, referring to FIG. 9, the processing for acquiring the first X-ray image set Ra in Step S2 of FIG. 7 will be described.

In Step S20, the image processing unit 5 acquires M pieces (four pieces) of the X-ray images 11 captured while translating the second grating 3 M times (four times) in a state in which no subject Q is arranged. One set of M pieces (4 pieces) of the X-ray images 11 acquired in Step S20 is the first X-ray image set Ra. Thereafter, the processing proceeds to Step S21.

In Step S21, the control unit 6 determines whether or not the fringe scanning has been performed a predetermined number of times. In other words, the control unit 6 determines whether or not the first X-ray image set Ra has been acquired by a predetermined number of sets. When the predetermined number of first X-ray image sets Ra has been acquired, the processing proceeds to Step S3. When the predetermined number of first X-ray image sets Ra has not been acquired, the processing returns to Step S20. As a result, j sets (10 sets) of first X-ray image sets Ra are obtained.

Figure 10:
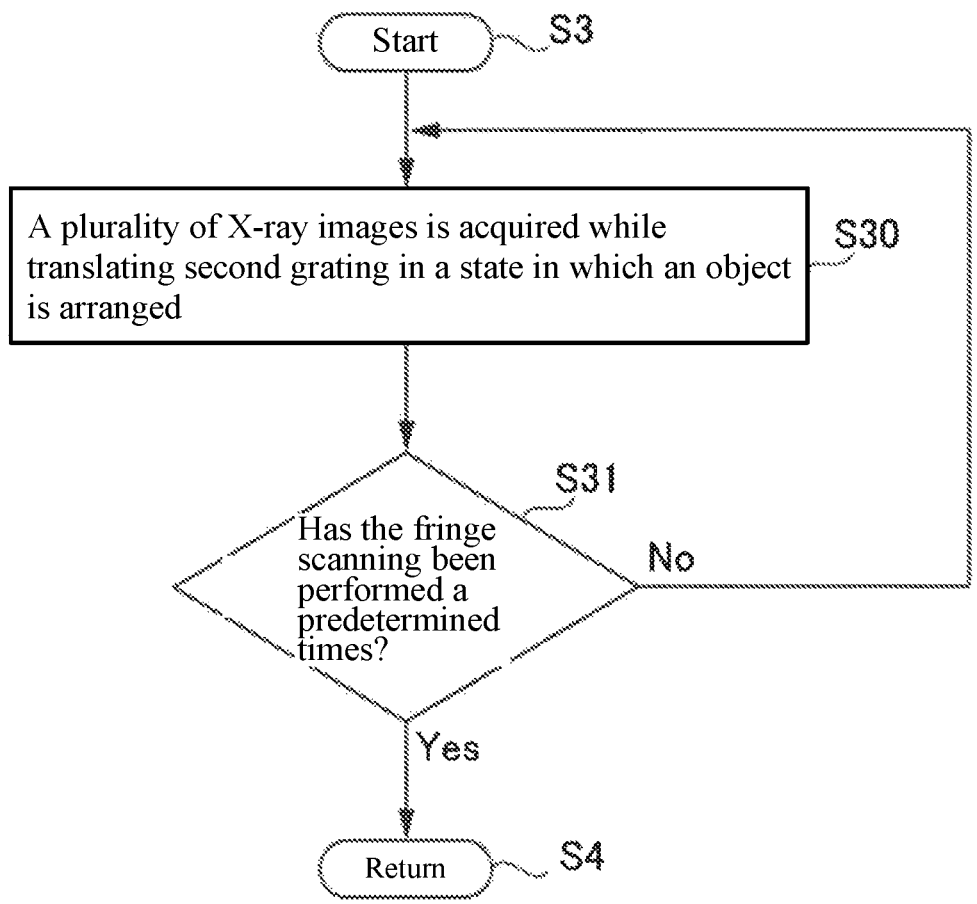
FIG. 10 is a schematic diagram for explaining second X-ray image set acquisition processing according to the first embodiment of the present invention.

Next, referring to FIG. 10, the processing of acquiring the second X-ray image set Rb in Step S3 of FIG. 7 will be described.

In Step S30, the image processing unit 5 acquires M pieces (four pieces) of the X-ray images 11 captured while translating the second grating 3 M times (four times) in a state in which a subject Q is arranged. One set of M pieces (4 pieces) of X-ray images 11 acquired in Step S30 is the second X-ray image set Rb. Thereafter, the processing proceeds to Step S31.

In Step S31, the control unit 6 determines whether or not the fringe scanning has been performed a predetermined number of times. In other words, the control unit 6 determines whether or not the second X-ray image set Rb has been acquired by the predetermined number of sets. When the predetermined number of the second X-ray image sets Rb is acquired, the processing proceeds to Step S4. When the predetermined number of the second X-ray image sets Rb has not been acquired, the processing returns to Step S30. As a result, j sets (300 sets) of the second X-ray image sets Rb are obtained.

Figure 11:
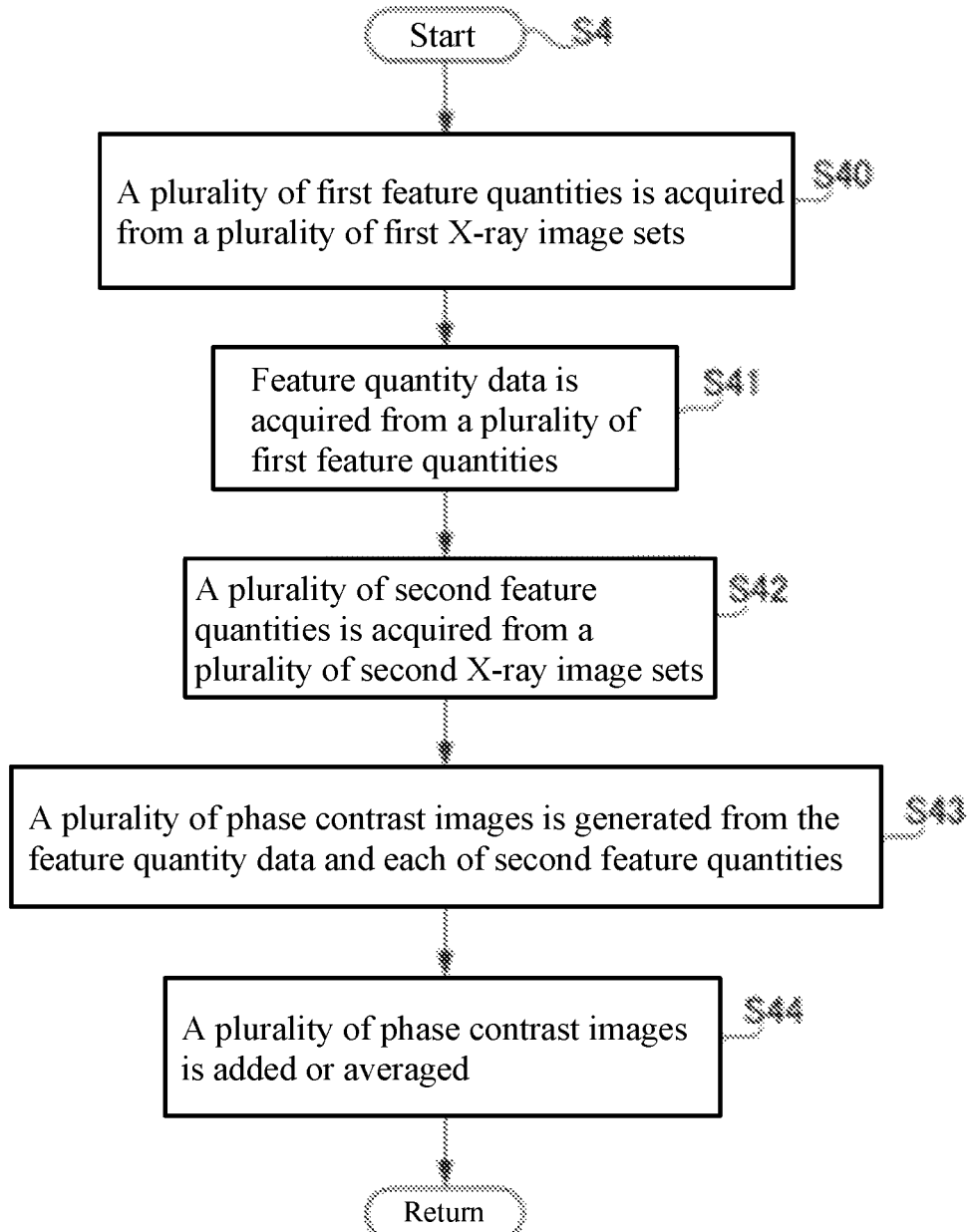
FIG. 11 is a schematic diagram for explaining phase-contrast image generation processing according to the first embodiment of the present invention.

Next, referring to FIG. 11, the processing in which the image processing unit 5 generates the phase-contrast image 15 in Step S4 of FIG. 7 will be described.

In Step S40, the image processing unit 5 acquires a plurality of first feature quantities 12 from the plurality of first X-ray image sets Ra based on the above expressions (2) to (4). Thereafter, in Step S41, the image processing unit 5 acquires one piece of the feature quantity data 13 from the plurality of first feature quantities 12 based on the above expressions (5) to (7). Thereafter, the processing proceeds to Step S42.

In Step S42, the image processing unit 5 acquires a plurality of second feature quantities 14 from a plurality of second X-ray image sets Rb based on the above expressions (9) to (11). Thereafter, in Step S43, the image processing unit 5 generates a plurality of phase-contrast images 15 from one piece of the feature quantity data 13 and each of the plurality of second feature quantities 14 based on the expressions (12) to (14). Thereafter, the processing proceeds to Step S44.

In Step S44, the image processing unit 5 acquires one phase-contrast image 15 by adding and averaging the plurality of phase-contrast images 15. Thereafter, the processing ends.

Effects of First Embodiment

In this first embodiment, the following effects can be acquired.

In the first embodiment, as described above, the X-ray phase image capturing system 100 is provided with the X-ray source 1, the plurality of gratings including the first grating 2 to be irradiated with the X-rays from the X-ray source 1 and the second grating 3 to be irradiated with the X-rays transmitted through the first grating 2, the detector 4 configured to detect the X-rays emitted from the X-ray source 1, the moving mechanism 8 configured to move the second grating 3, and the image processing unit 5 configured to generate the phase-contrast image 15 from the X-ray image set R including the plurality of X-ray images 11 detected by the detector 4. The image processing unit 5 is configured to extract the respective feature quantities 12 (and feature quantities 14) including at least one of the amplitude, the average pixel value intensity, and the phase from the plurality of X-ray image sets R acquired by performing the fringe scanning a plurality of times in a short time, and generate the phase-contrast image 15 based on the extracted plurality of feature quantities 12 (and feature quantities 14). As a result, it is possible to shorten the time duration of performing single fringe scanning of performing the imaging while translating the second grating 3 by one period of the period p2 of the second grating 3, and therefore, it is possible to suppress the change in the relative position between the self-image that occurs during the fringe scanning and the second grating 3. As a result, it is possible to suppress the change in the waveform 10 of the acquired intensity change, which in turn can suppress deterioration of the image quality of the generated phase-contrast image 15.

Further, in the first embodiment, as described above, the image processing unit 5 is configured to generate the phase-contrast image 15 based on the plurality of feature quantities 12 (and feature quantities 14) extracted from the X-ray image set R acquired by performing the fringe scanning a plurality of times in a short time within a range in which the imaging condition does not substantially change due to heat between the plurality of X-ray images 11. As a result, the fringe scanning can be performed within a time range in which the imaging condition does not substantially change due to heat. As a result, it is possible to suppress deterioration of the image quality of the phase-contrast image 15 caused by the change of the imaging condition due to heat.

Also, in the first embodiment, as described above, the X-ray phase image capturing system 100 is configured to generate the phase-contrast image 15 based on the plurality of feature quantities 12 (and feature quantities 14) extracted from the X-ray image set R acquired by performing a plurality of fringe scanning in a short time of 100 seconds or less. As a result, since the X-ray image set R is acquired in a short time of 100 seconds or less, it is possible to minimize the effects of the change in the imaging condition caused by heat at the time of performing the fringe scanning. As a result, it is possible to further suppress the change in the waveform 10 of the acquired intensity change, which in turn can further suppress deterioration of the image quality of the acquired phase-contrast image 15.

In the first embodiment, as described above, the image processing unit 5 is configured to acquire the plurality of first feature quantities 12 from the plurality of first X-ray image sets Ra captured by performing the plurality of fringe scanning in a short time without arranging a subject Q, acquire the plurality of second feature quantities 14 from the plurality of second X-ray image sets Rb captured by performing a plurality of fringe scanning in a short time while arranging a subject Q, and generate the phase-contrast image 15 using at least one of the plurality of the first feature quantities 12 and at least one of the plurality of the second feature quantities 14. As a result, since the fringe scanning is performed in a short time, the first feature quantities 12 and the second feature quantities 14 acquired in a state in which the change of the imaging condition is not substantially received due to the heat generated during the acquisition of the X-ray image set R. As a result, the first feature quantities 12 and the second feature quantities 14 can be made as less susceptible to the change in the imaging condition caused by the heat generated during the acquisition of the X-ray image set R as much as possible, and therefore, deterioration of the image quality of the generated phase-contrast image 15 can be further suppressed.

In the first embodiment, as described above, the image processing unit 5 is configured to acquire one piece of the feature quantity data 13 from the plurality of first feature quantities 12 and generate the phase-contrast image 15 using one piece of the feature quantity data 13 and the plurality of second feature quantities 14. As a result, since the feature quantity data 13 is acquired from the plurality of the first feature quantities 12 having a short exposure time (charge accumulation time) in order to perform the imaging in a short time, the quantum noise becomes smaller than the quantum noise of each of the plurality of first feature quantities 12, and therefore the feature quantity contrast can be more provided. Then, the phase-contrast image 15 can be generated by using the feature quantity data 13 and the second feature quantities 14 which are more contrasted than each of the plurality of first feature quantities 12. As a result, the feature quantity data 13 sharper in the feature quantity contrast than each of the plurality of first feature quantities 12 captured in a short time can be used, so that the image quality of the generated phase-contrast image 15 can be improved.

Further, in the first embodiment, as described above, the image processing unit 5 is configured to acquire the feature quantity data 13 by adding and averaging the plurality of first feature quantities 12. As a result, the feature quantity data 13 can be easily acquired from the plurality of first feature quantities 12 captured in a short time.

Also, in the first embodiment, as described above, the image processing unit 5 is configured to generate the phase-contrast image 15 based on each of the plurality of second feature quantities 14 and the feature quantity data 13. With this, the phase-contrast image 15 can be generated using the feature quantity data 13 and each of the plurality of second feature quantities 14. As a result, for example, the image quality of the phase-contrast image 15 generated from each of the plurality of second feature quantities 14 can be improved as compared with the case where the phase-contrast image 15 is generated using each of the first feature quantities 12 and each of the plurality of second feature quantities 14.

Also, in the first embodiment, as described above, the image processing unit 5 is configured to add or average the phase-contrast image 15 generated based on each of the plurality of second feature quantities 14 and the feature quantity data 13. This allows a single phase-contrast image 15 to be generated from the plurality of phase-contrast images 15 generated based on the plurality of second feature quantities 14 captured in a short time. As a result, for example, even in cases where the imaging is performed with a long exposure time, the fringe scanning can be performed a plurality of times in a short time as compared with the phase-contrast image 15 captured by single fringe scanning, so that the effects of the change in the imaging condition caused by heat can be suppressed from accumulating.

Further, in the first embodiment, as described above, it further includes the control unit 6 for controlling the movement of the grating by the moving mechanism 8, the control unit 6 is configured to determine the time for performing the fringe scanning based on the period p2 of the second grating 3 moved by the moving mechanism 8. Thus, for example, in cases where the period p2 of the second grating 3 for the translational movement is 10 m, it is possible to perform the fringe scanning with an appropriate time based on the period p2 of the second grating 3, such as making scanning time a short time of 10 seconds. As a result, the fringe scanning can be performed at a relative position between the self-image and the plurality of gratings within a time range in which influences due to positional deviations other than positional deviations due to the translational movement of the second grating 3 can be sufficiently suppressed, and the exposure time can be ensured as much as possible. Therefore, deterioration of the image quality can be further reduced.

Also, in the first embodiment, as described above, the image processing unit 5 is configured to acquire the moving speed of the focal point of the X-ray source 1 based on the position of the position reference portion 16 reflected in each of the X-ray images 11. The control unit 6 is configured to determine the time for performing the fringe scanning based on the acquired moving speed of the focal point of the X-ray source 1. Thus, the movement of the focal point of the X-ray source 1 can be detected based on the position of the position reference portion 16 reflected in the X-ray image 11. As a result, even in cases where the focal point of the X-ray source 1 has moved, the fringe scanning can be performed within a time range in which the effects of the movements of the focal point of the X-ray source 1 can be sufficiently suppressed, and the exposure time can be secured as much as possible, so that deterioration of the image quality of the phase-contrast image 15 caused by the movements of the self-image due to the movements of the focal point of the X-ray source 1 can be suppressed.

Second Embodiment

Figure 14:
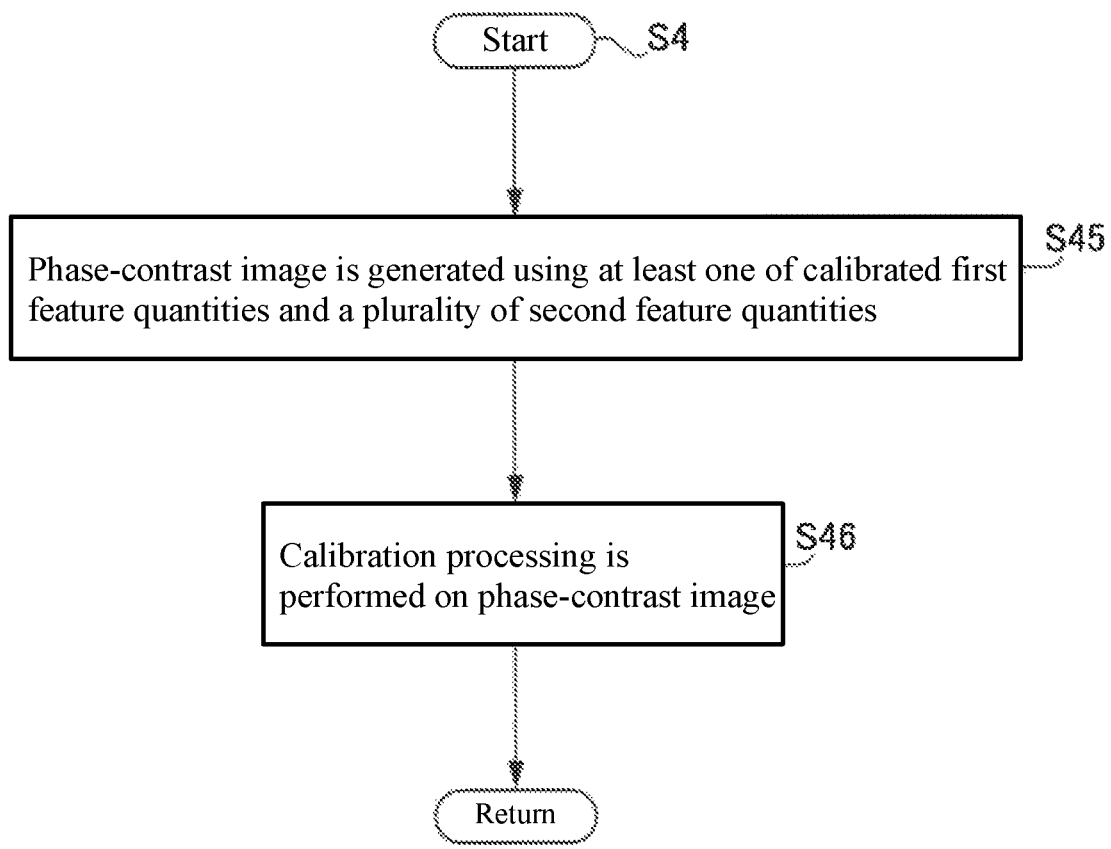
FIG. 14 is a schematic diagram for explaining phase-contrast image generation processing according to the second embodiment of the present invention.

Next, referring to FIG. 1 and FIG. 14, an X-ray phase image capturing system 200 according to a second embodiment of the present invention will be described. Unlike the first embodiment in which a plurality of X-ray image sets R is acquired, the first feature quantities 12, the feature quantity data 13, and the second feature quantities 14 are acquired from the plurality of X-ray image set R, and the phase-contrast image 15 is generated, in the second embodiment, the image processing unit 5 is configured to concurrently perform the extraction and calibration processing of the feature quantities 12 (and feature quantities 14) from the X-ray image set R in the fringe scanning and the acquisition of the X-ray image set R in the subsequent fringe scanning. Note that the same component as that of the above first embodiment is denoted by the same reference numeral, and the description thereof is omitted.

In the second embodiment, the image processing unit 5 is configured to concurrently perform the extraction and calibration processing of the feature quantities 12 (and feature quantities 14) from the X-ray image set R in the fringe scanning and the acquisition of the X-ray image set R in the subsequent fringe scanning. Further, in the second embodiment, the image processing unit 5 is configured to perform, as the calibration processing, unwrap processing for continuing the discontinuous points of the phase caused by the phase reflection on the phase differential image 15b. Further, the image processing unit 5 is configured to perform brightness calibration for calibrating the change in the X-ray image 11 detected by the detector 4 including at least the change in the dose of the X-rays emitted from the X-ray source 1, as the calibration processing. Specifically, luminance calibration is performed as follows.

The X-ray image 11 in the image region having no first grating 2 and second grating 3 is used as a brightness calibration image 110. Further, the X-ray image 11 captured by arranging a subject Q is used as a brightness calibration image 111. The pixel value in the brightness calibration image 110 is $I^{air\_bright}_{jk}(x, y)$, the pixel value in the brightness calibration image 111 is $I^{obj\_bright}_{jk}(x, y)$, and the average value of the pixel values of the entire image $I^{air\_bright}_{jk}(x, y)$ and $I^{obj\_bright}_{jk}(x, y)$ as $B^{air}_{jk}$, $B^{obj}_{jk}$, respectively, the following expressions (15) and (16) are acquired.

$$B^{air}_{jk} = \sum_{x,y}^{all\,area} I^{air\_bright}_{jk}(x, y)/n_x n_y \quad (15)$$

$$B^{obj}_{jk} = \sum_{x,y}^{all\,area} I^{obj\_bright}_{jk}(x, y)/n_x n_y \quad (16)$$

where, $n_x$, $n_y$ is the number of pixels in the X-direction and Y-direction in the image 110 for brightness calibration and the image 111 for brightness calibration. Also, the average pixel value B of the first Step (k=1) in the first picture (j=1) is $B_{11}$.

Next, the luminance calibration coefficients is defined as shown in $C^{air}_{jk}$, $C^{obj}_{jk}$ below.

$$C^{air}_{jk}=B^{air}_{11}/B^{air}_{jk} \quad (17)$$

$$C^{obj}_{jk}=B^{air}_{11}/B^{obj}_{jk} \quad (18)$$

That is, as shown in the expressions (17) and (18), the luminance calibration coefficients are determined based on the average pixel value $B_{11}$ of the first Step of the first image captured without arranging a subject Q.

After the brightness is calibrated, the X-ray image 11 captured without arranging a subject Q and the X-ray image 11 captured by arranging a subject Q can be represented by the following expressions (19) and (20), respectively.

$$I^{air}_{jk}(x,y)C^{air}_{jk} \quad (19)$$

$$I^{obj}_{jk}(x,y)C^{obj}_{jk} \quad (20)$$

Then, the expressions (1) and (8) used in the first embodiment can be rewritten as the following expressions (21) and (22), respectively.

$$S^{air}_j(x, y) = \sum_{k=1}^{M} I^{air}_{jk}(x, y)C^{air}_{jk}\exp\left(-\frac{2i\pi k}{M}\right) \quad (21)$$

$$S^{obj}_j(x, y) = \sum_{k=1}^{M} I^{obj}_{jk}(x, y)C^{obj}_{jk}\exp\left(-\frac{2i\pi k}{M}\right) \quad (22)$$

In the second embodiment, the image processing unit 5 is configured to replace $S^{air}_j(x, y)$ and $S^{obj}_j(x, y)$ of the expression used in the first embodiment with the expression (21) and $S^{air}_j(x, y)$ and $S^{obj}_j(x, y)$ of the expression (21) to generate a phase-contrast image 15 by the same processing as the first embodiment.

(Generation Processing of Phase-Contrast Image)

Next, referring to FIG. 7 and FIG. 12 to FIG. 14, a method of generating a phase-contrast image 15 according to the second embodiment will be described.

Figure 12:
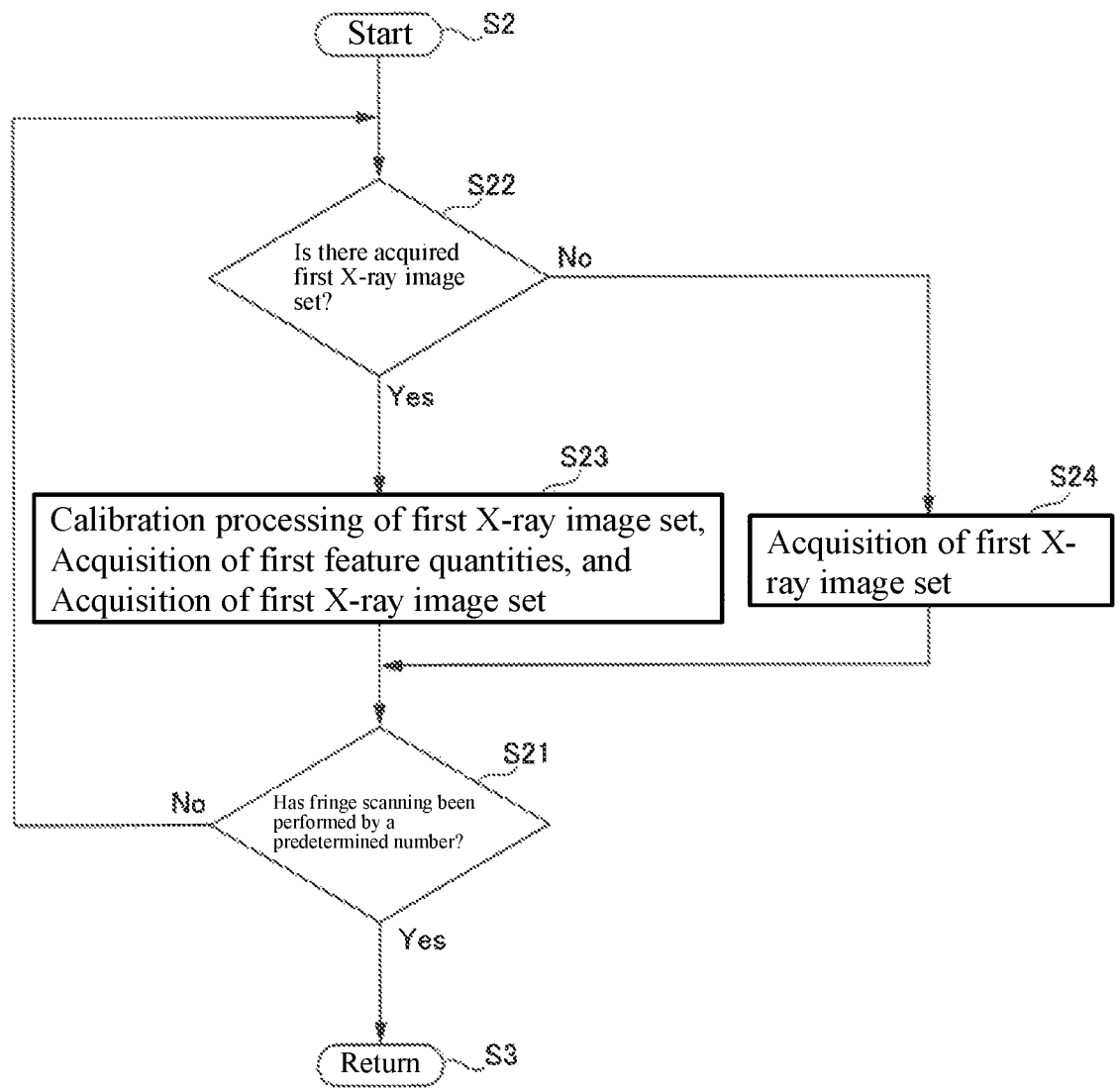
FIG. 12 is a schematic diagram for explaining first X-ray image set acquisition processing according to a second embodiment of the present invention.

First, referring to FIG. 12, the acquisition processing of the first X-ray image set Ra in Step S2 of FIG. 7 will be described.

In Step S22, the control unit 6 confirms whether or not there is a first X-ray image set Ra already acquired. If there is a first X-ray image set Ra already acquired, the processing proceeds to Step S23. If there is no first X-ray image set Ra already acquired, the processing proceeds to Step S24.

In Step S23, the image processing unit 5 performs the calibration processing for each X-ray image 11 in the first X-ray image set Ra. Thereafter, the image processing unit 5 acquires a plurality of first feature quantities 12 from a plurality of first X-ray image sets Ra to which the calibration processing has been performed. Further, in Step S23, the image processing unit 5 performs the acquisition of the subsequent first X-ray image set Ra concurrently with the calibration processing of each X-ray image 11 of the first X-ray image set Ra and the acquisition of the first feature quantities 12. In Step S24, the image processing unit 5 performs the acquisition of the first X-ray image sets Ra. Since the acquisition processing of the first X-ray image set Ra in Step S23 and Step S24 is the same as in Step S2 in the aforementioned first embodiment, the detailed explanation will be omitted.

Thereafter, the processing proceeds to Step S21 and, in a case where a predetermined number of sets (j sets) of the first X-ray image set Ra has been acquired, the processing proceeds to the acquisition processing (Step S3) of the second X-ray image set Rb.

Figure 13:
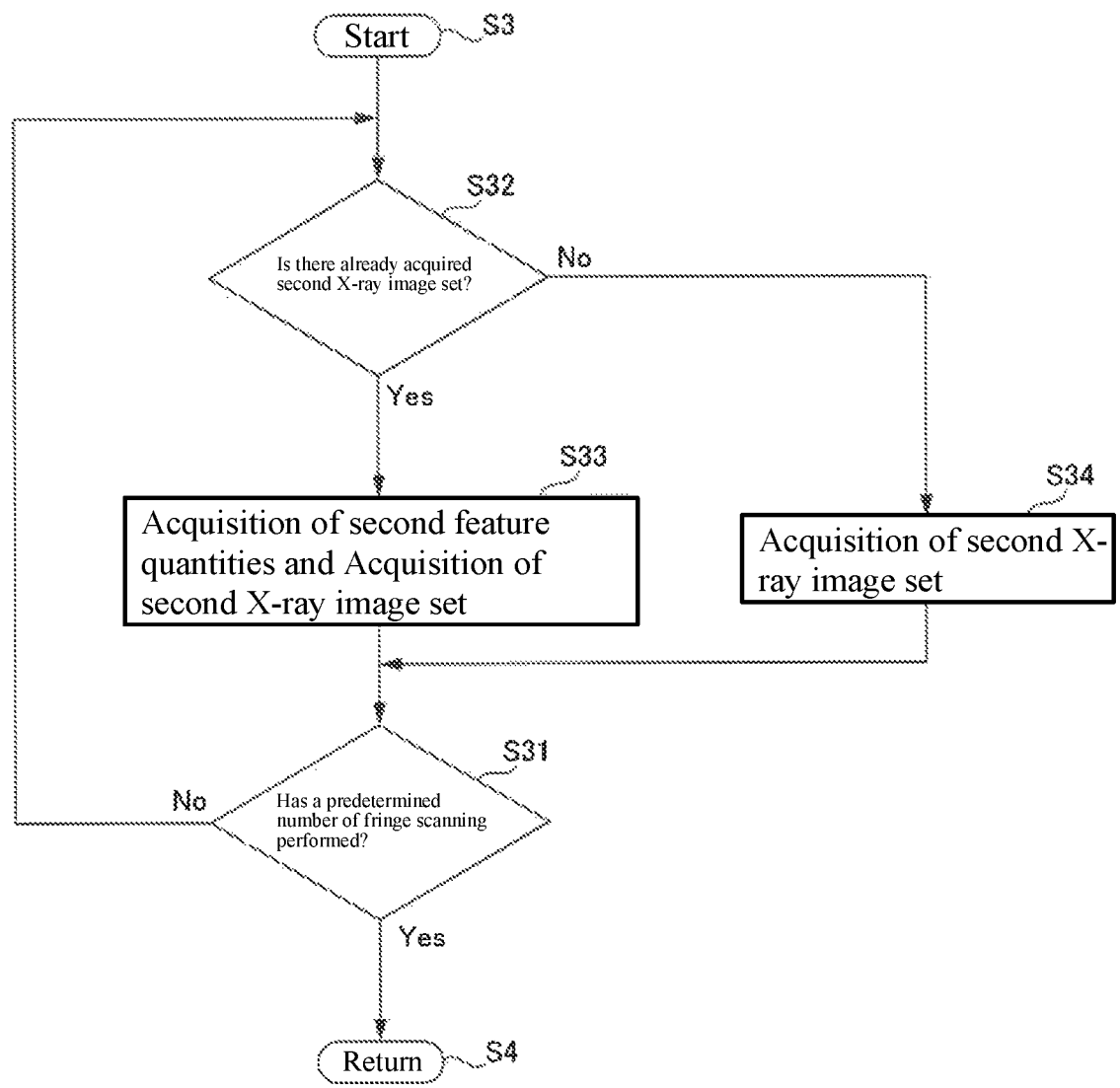
FIG. 13 is a schematic diagram for explaining second X-ray image set acquisition processing according to the second embodiment of the present invention.

Next, referring to FIG. 13, the processing for acquiring the second X-ray image set Rb in Step S3 of FIG. 7 will be described.

In Step S32, the image processing unit 5 acquires a plurality of second feature quantities 14 from a plurality of second X-ray image sets Rb. In Step S33, the image processing unit 5 acquires the subsequent second X-ray image set Rb in parallel with the acquisition of the second feature quantities 14. In Step S34, the image processing unit 5 performs the acquisition of the second X-ray image set Rb. Since the acquisition processing of the second X-ray image set Rb in Step S33 and Step S34 is the same as that in Step S3 in the aforementioned first embodiment, the detailed explanation will be omitted.

Thereafter, the processing proceeds to Step S31 and, in a case where a predetermined number of sets (j sets) of the second X-ray image sets Rb has been acquired, the processing proceeds to the generation processing (Step S4) of the phase-contrast image 15.

Next, referring to FIG. 14, the generation processing of the phase-contrast image 15 in Step S4 of FIG. 7 will be described.

In Step S45, the image processing unit 5 generates a phase-contrast image 15 using at least one or more of a plurality of corrected first feature quantities 12 and a plurality of corrected second feature quantities 14. Thereafter, the processing proceeds to Step S46.

In Step S46, the image processing unit 5 performs the calibration processing on the generated phase-contrast image 15 and terminates the processing.

In the second embodiment, the image processing unit 5 is configured to perform the calibration processing of the plurality of X-ray images 11 included in the first X-ray image set Ra, the acquisition of the plurality of first feature quantities 12, and the acquisition of the subsequent first X-ray image set Ra in parallel. In the second embodiment, the image processing unit 5 is configured to perform the acquisition of the second feature quantities 14 and the acquisition of the subsequent second X-ray image set Rb in parallel.

The rest of the configuration of the second embodiment is the same as that of the aforementioned first embodiment.

Effects of Second Embodiment

In the second embodiment, the following effects can be acquired.

In the second embodiment, as described above, the image processing unit 5 is configured to perform the extraction and the calibration processing of the feature quantities 12 (and feature quantities 14) from the X-ray image set R in the fringe scanning and the acquisition of the X-ray image set R in the subsequent fringe scanning in parallel. This allows the extraction and the calibration processing of the feature quantities 12 (and feature quantities 14) from the X-ray image set R and the acquisition of the X-ray image set R in the subsequent fringe scanning in parallel. Therefore, the production efficiency of the phase-contrast image 15 can be improved as compared with the case in which the extraction of the feature quantities 12 (and feature quantities 14), the calibration processing, and the generation of the phase-contrast image 15 are performed every time the X-ray image set R is acquired.

Also, in the second embodiment, as described above, the phase-contrast image 15 includes a phase differential image 15b, and the image processing unit 5 is configured to perform, as calibration processing, unwrap processing for continuing phase discontinuous points caused by the phase reflection on the phase differential image 15b. Note that phase discontinuous points are likely to occur at boundaries between a subject Q and its background. Therefore, by performing unwrap processing, it is possible to eliminate the discontinuous points of the phase caused by phase reflection. As a result, even in cases where the position at which a subject Q is reflected differs in the respective X-ray images 11, it is possible to suppress the phase discontinuous points from being synthesized, which in turn can suppress deterioration of the image quality of the generated phase differential image 15b.

Further, in the second embodiment, as described above, the image processing unit 5 is configured to perform, as a calibration processing, brightness calibration for calibrating a change in the X-ray image 11 detected in the detector 4 including at least the change in the dose of X-rays emitted from the X-ray source 1. As a result, it is possible to calibrate an artifact A caused in accordance with the change in the X-ray image 11 due to the imaging device such as the detector 4 due to a short imaging period. As a result, even in cases where one phase-contrast image 15 is generated from a plurality of phase-contrast images 15, an artifact A due to the imaging device such as the detector 4 generated in each phase-contrast image 15 due to the short imaging time can be corrected, so that deterioration of the image quality of the phase-contrast image 15 due to the accumulation of artifacts A caused by the change in the X-ray image 11 due to the imaging device such as the detector 4 can be suppressed.

The other effects of the second embodiment are the same as those of the aforementioned first embodiment.

(Modifications)

It should be noted that the embodiment disclosed herein is to be considered in all respects as illustrative and not restrictive. The scope of the present invention is indicated by the appended claims rather than by the foregoing embodiment descriptions and includes all modifications (changes) within the meanings and ranges equivalent to the scope of the claims.

Figure 15:
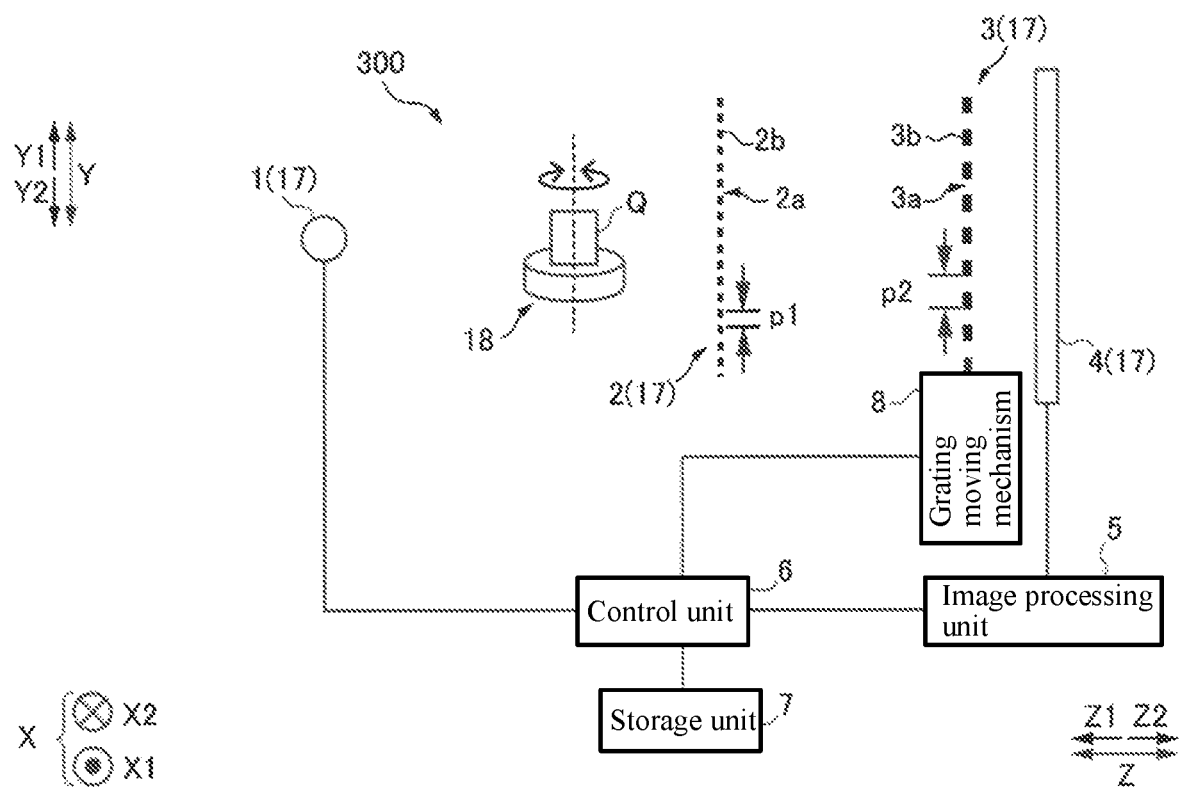
FIG. 15 is a schematic diagram of an X-ray phase image capturing system according to a first modification of the first embodiment of the present invention as viewed from the X-direction.

For example, in the first and second embodiments described above, an example is described in which imaging is performed with a subject Q fixed, but the present invention is not limited thereto. For example, as shown in the X-ray phase image capturing system 300 of FIG. 15, it may be configured such that the system further includes a rotating mechanism 18 configured to relatively rotate an imaging system 17 composed of an X-ray source 1, a detector 4, and a plurality of gratings and a subject Q and that the image processing unit 5 generates a three-dimensional phase-contrast image from a plurality of phase-contrast images 15 captured in a plurality of rotation angles while relatively rotating the subject Q and the imaging system 17. With this configuration, it is possible to generate a three-dimensional phase-contrast image by using the respective phase-contrast images 15 in which deterioration of the image quality caused by the change of the imaging condition due to heat can be suppressed. As a result, it is possible to effectively suppress deterioration of the image quality of the three-dimensional phase-contrast image to be generated even in the case of acquiring a three-dimensional phase-contrast image in which the imaging time becomes long and the effects of the change in the imaging condition due to heat is likely to occur. Note that the rotating mechanism 18 is configured to relatively rotate the subject Q and the imaging system 17 based on the signal from the control unit 6. The rotating mechanism 18 includes, for example, a rotating stage driven by a motor or the like.

Figure 16:
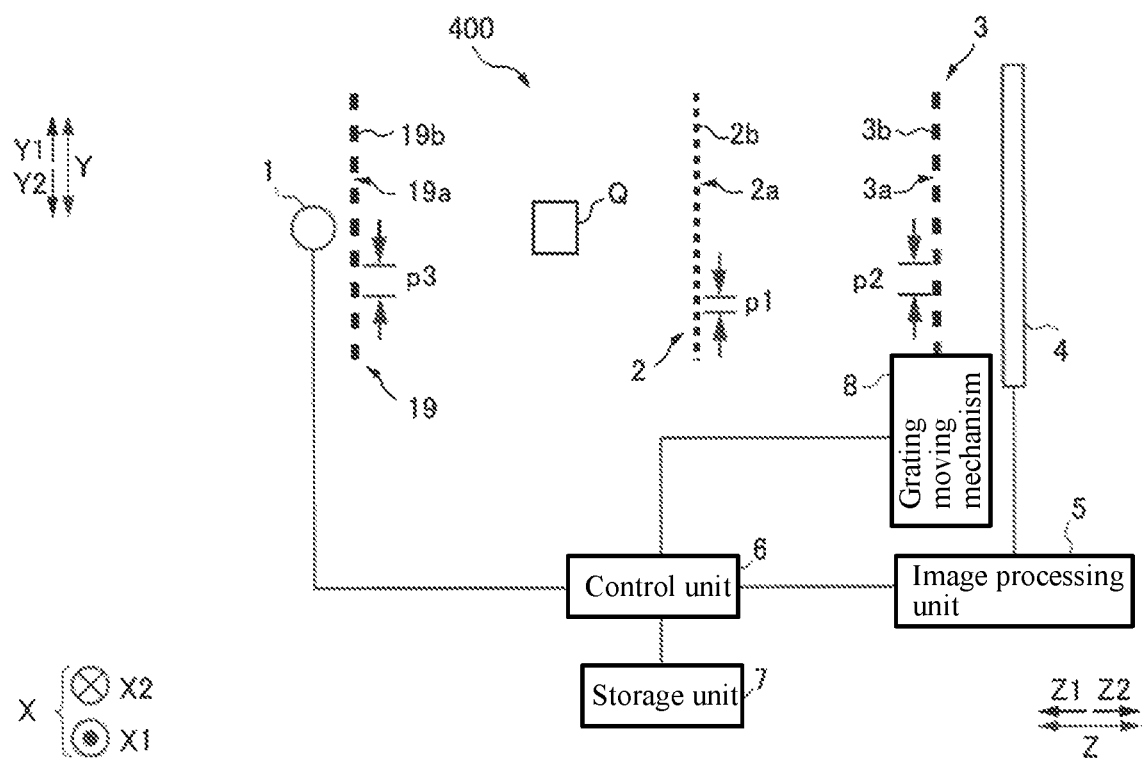
FIG. 16 is a schematic diagram of an X-ray phase image capturing system according to a second modification of the first embodiment of the present invention as viewed from the X-direction.

In the above-mentioned first and second embodiment, although an example is shown in which the first grating 2 and the second grating 3 are provided as a plurality of gratings have been described, the present invention is not limited to this. For example, as shown in the X-ray phase image capturing system 400 shown in FIG. 16, a third grating 19 may be provided between the X-ray source 1 and the first grating 2. The third grating 19 has a plurality of slits 19a and X-ray absorption portions 19b arranged in the Y-direction at a predetermined period (pitch) p3. The slit 19a and the X-ray absorption portion 19b are each formed so as to extend linearly. The slit 19a and the X-ray absorption portion 19b are each formed so as to extend in parallel with each other. The third grating 19 is arranged between the X-ray source 1 and the first grating 2, and the X-rays are emitted from the X-ray source 1. The third grating 19 is configured so that the X-rays passing through each slit 19a are the ray light sources corresponding to the positions of each slit 19a. Thereby, the coherence of X-rays irradiated from X-ray source 1 by the third grating 19 can be enhanced. As a result, since the self-image of the first grating 2 can be formed without depending on the focal diameter of the X-ray source 1, the degree of flexibility in selecting the X-ray source 1 can be improved. In addition, since the third grating 19 uses the X-rays that have passed through each slit 19a as a line light source corresponding to the position of each slit 19a, even when the focal point of X-ray source 1 is moved, each focal point of the X-rays emitted from each slit 19a is not moved unless the third grating 19 is moved, so that the self-image of the first grating 2 is not moved. Therefore, the change in the imaging condition caused by the movements of the focal point of the X-ray source 1 can be made less susceptible, so that deterioration of the image quality of the generated phase-contrast image 15 can be further suppressed.

In the first and second embodiment, although the phase grating is used as the first grating 2, the present invention is not limited to this. For example, an absorption grating may be used as the first grating 2. When an absorption grating is used as the first grating 2, the image processing unit 5 generates a phase-contrast image 15 by a striped pattern of X-rays transmitted through the first grating 2 and the second grating 3. Accordingly, since the phase-contrast image 15 can be acquired without using the self-image of the first grating 2, the flexibility of the positioning position of the first grating 2 can be improved. However, when the absorption grating is used as the first grating 2, the image quality of the acquired phase-contrast image 15 deteriorates, and therefore, when it is desired to acquire a high-quality phase-contrast image 15, it is preferable to use the phase grating as the first grating 2.

In the above-mentioned second embodiment, the unwrap processing and the brightness are calibrated by way of the calibration processing, but the present invention is not limited to this. For example, the image processing unit 5 may be configured to perform offsetting processing or missing processing as the calibration processing.

In the first and second embodiment, an example is shown in which the moving mechanism 8 causes the translation movements of the second grating 3, but the present invention is not limited to this. The first grating 2 may be translated. The grating to be moved may be any grating.

DESCRIPTION OF SYMBOLS

1: X-ray source
2: First grating
3: Second grating
4: Detector
5: Image processing unit
8: Moving mechanism
11: X-ray image
12: First feature quantity (feature quantity)
13; Feature quantity data
14: Second feature quantity (feature quantity)
15: phase-contrast image
16: Position reference portion
17: Imaging system
18: Rotating mechanism
19: Third grating
100, 200, 300, 400: Line phase imaging system
Q: Subject
R: X-ray image set
p2: Period of grating

The invention claimed is:

1. An X-ray phase image capturing system comprising:
an X-ray source;
a plurality of gratings including a first grating to be irradiated with X-rays from the X-ray source and a second grating to be irradiated with the X-rays transmitted through the first grating;
a detector configured to detect the X-rays emitted from the X-ray source;
a moving mechanism configured to move at least one of the plurality of gratings;
an image processing unit configured to generate a phase-contrast image from an X-ray image set including a plurality of X-ray images detected by the detector,
wherein the image processing unit is configured to:
extract, from a plurality of X-ray image sets acquired by performing fringe scanning multiple times within a time range in which an imaging condition change due to heat between the plurality of X-ray images does not substantially occur, a plurality of feature quantities including an amplitude, average pixel value intensity, and/or a phase; and
generate the phase-contrast image based on the plurality of feature quantities extracted.

2. The X-ray phase image capturing system as recited in claim 1
wherein the image processing unit is configured to:
acquire, as a plurality of first feature quantities, the plurality of feature quantities from a plurality of X-ray image sets acquired by performing fringe scanning a plurality of times in the time range without arranging a subject;
acquire, as a plurality of second feature quantities, the plurality of feature quantities from a plurality of X-ray image sets acquired by performing fringe scanning a plurality of times in the time range while arranging a subject; and
generate the phase-contrast image using at least one of the plurality of first feature quantities and at least one of the plurality of second feature quantities.

3. The X-ray phase image capturing system as recited in claim 2, wherein the image processing unit is configured to acquire one piece of feature quantity data from the plurality of first feature quantities and generate the phase-contrast image using the one piece of feature quantity data and the plurality of second feature quantities.

4. The X-ray phase image capturing system as recited in claim 3,
wherein the image processing unit is configured to acquire the feature quantity data by adding or averaging the plurality of first feature quantities.

5. The X-ray phase image capturing system as recited in claim 3,
wherein the image processing unit is configured to generate the phase-contrast image based on each of the plurality of second feature quantities and the feature quantity data.

6. The X-ray phase image capturing system as recited in claim 3
wherein the image processing unit is configured to add or average the phase-contrast images generated based on each of the plurality of second feature quantities and the feature quantity data.

7. The X-ray phase image capturing system as recited in claim 1,
wherein the image processing unit is configured to perform extraction and calibration processing of the feature quantities from the X-ray image set in fringe scanning and acquisition of the X-ray image set in subsequent fringe scanning in parallel.

8. The X-ray phase image capturing system as recited in claim 7,
wherein the phase-contrast image includes a phase differential image, and
wherein the image processing unit is configured to perform, as the calibration processing, unwrap processing for continuing phase discontinuous points caused by phase reflection on the phase differential image.

9. The X-ray phase image capturing system as recited in claim 7,
wherein the image processing unit is configured to perform, as the calibration processing, a brightness calibration for calibrating a change in the X-ray image detected by the detector including at least a change in a dose of the X-rays irradiated from the X-ray source.

10. The X-ray phase image capturing system as recited in claim 1, further comprising:
a control unit configured to control a grating movement in the moving mechanism,
wherein the control unit is configured to determine a time for performing fringe scanning based on a period of the grating moved by the moving mechanism.

11. The X-ray phase image capturing system as recited in claim 10,
wherein the control unit is configured to acquire a moving speed of a focal point of the X-ray source based on a position of a position reference portion reflected in each of X-ray images and determine a time of performing the fringe scanning based on the moving speed of the acquired focal point of the X-ray source.

12. The X-ray phase image capturing system as recited in claim 1, further comprising:
a rotating mechanism configured to relatively rotate an imaging system composed of an X-ray source, a detector, and a plurality of gratings and a subject,
wherein the image processing unit is configured to generate a three-dimensional phase-contrast image from a plurality of phase-contrast images captured at a plurality of rotation angles while relatively rotating a subject and the imaging system.

13. The X-ray phase image capturing system as recited in claim 1,
wherein the plurality of gratings further includes a third grating arranged between the X-ray source and the first grating.

* * * * *